United States Patent
May et al.

(10) Patent No.: US 7,247,465 B2
(45) Date of Patent: Jul. 24, 2007

(54) SCREENING PROCESS FOR HYDANTOIN RACEMASES

(75) Inventors: Oliver May, Frankfurt (DE); Karlheinz Drauz, Freigericht (DE); Stefan Buchholz, Hanau (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/559,434

(22) PCT Filed: May 15, 2004

(86) PCT No.: PCT/EP2004/005239

§ 371 (c)(1),
(2), (4) Date: Dec. 5, 2005

(87) PCT Pub. No.: WO2004/111227

PCT Pub. Date: Dec. 23, 2004

(65) Prior Publication Data

US 2006/0210989 A1    Sep. 21, 2006

(30) Foreign Application Priority Data

Jun. 6, 2003 (DE) ................. 103 26 109
May 5, 2004 (DE) ...................... 10 2004 022 065

(51) Int. Cl.
*C12N 9/88* (2006.01)
*C12P 1/00* (2006.01)
*C12P 13/04* (2006.01)

(52) U.S. Cl. ................. 435/232; 435/4; 435/6; 435/69.1; 435/183; 435/41; 435/106

(58) Field of Classification Search .............. 435/4, 435/6, 69–1, 183, 232, 41, 106; 536/23–2
See application file for complete search history.

(56) References Cited

U.S. PATENT DOCUMENTS

| | | | |
|---|---|---|---|
| 4,912,044 A | 3/1990 | Jacob et al. | |
| 5,523,224 A | 6/1996 | Burtscher et al. | |
| 5,707,837 A | 1/1998 | Drauz et al. | |
| 6,087,136 A | 7/2000 | Gohkale et al. | |
| 6,403,357 B1 | 6/2002 | Hsu et al. | |
| 6,713,288 B1 | 3/2004 | Altenbuchner et al. | |
| 6,767,725 B2 | 7/2004 | Bommarius et al. | |
| 7,060,485 B2 | 6/2006 | Takenaka et al. | |
| 7,098,019 B2 | 8/2006 | Takenaka et al. | |
| 2002/0102713 A1 | 8/2002 | Suzuki et al. | |
| 2003/0059816 A1 | 3/2003 | Fotheringham et al. | |
| 2003/0175910 A1 | 9/2003 | Altenbuchner et al. | |

OTHER PUBLICATIONS

Siemann et al., J. Mol. Catalysis (B. Enzymatic) 6:387-397 (1998).
Hils, et al., *Applied Microbiology and Biotechnology* 57(5-6):680-688 (2001).
Pietzsch, et al., Ann. N. Y. Acad. Sci. 672 (*Enzyme Engineering XI*), 478-83 (1992).
Lickefett, et al., Tetrahedron: Asymmetry 4(6), 1129-35 (1993).
Watabe, et al., *J. Bacteriol.* 174(24):7989-95) (1992).
Soong, et al., Journal of Molecular Catalysis B: Enzymatic 12(1-6):61-70 (2001).
Wiese, et al., Applied Microbiology and Biotechnology 55(6):750-757 (2001).
Yin, et al., Process Biochemistry (Oxford) 35(9): 915-921 (2000).
Park, Applied Biochemistry and Biotechnology 81(1):53-65 (1999).
Pozo, Journal of Applied Microbiology 92(6):1028-1034 (2002).
Chung, et al., Enzyme and Microbial Technology 30(7):867-874 (2002).
Las Heras-Vazquez, Biochemical and Biophysical Research Communications 303(2):541-547 (2003).

*Primary Examiner*—Manjunath N. Rao
(74) *Attorney, Agent, or Firm*—Michael A. Sanzo; Law Office of Michael A. Sanzo, LLC

(57) ABSTRACT

The present invention relates to a screening process for hydantoin racemases and to novel hydantoin racemases, to the nucleic acid sequences coding therefor and to a proces for mutagenesis.

Figure 1:
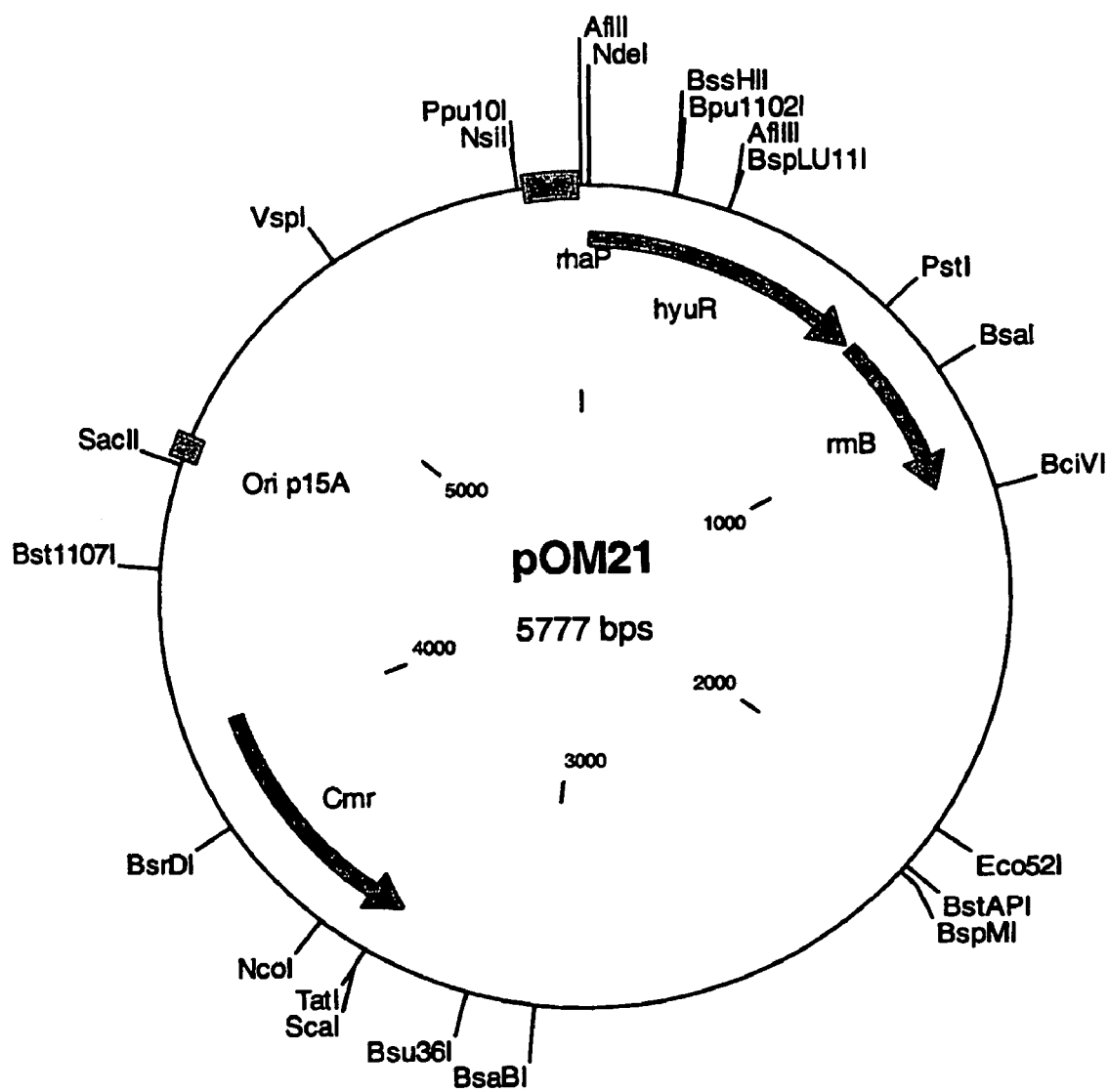

Hydantoin racemases are of interest in connection with the production of enantiomerically enriched amino acids from racemic hydantoins.

20 Claims, 4 Drawing Sheets

Fig: 3

SEQUENCE LISTING

```
<160> NUMBER OF SEQ ID NOS: 16

<210> SEQ ID NO 1
<211> LENGTH: 6
<212> TYPE: PRT
<213> ORGANISM: Artificial sequence
<220> FEATURE:
<223> OTHER INFORMATION: consensus sequence found in hydantoin racemase
      sequence of Arthrobacter crystallopoietes
<220> FEATURE:
<221> NAME/KEY: misc_feature
<222> LOCATION: (2)..(2)
<223> OTHER INFORMATION: Xaa is an amino acid selected from A, R, N, D,
      C, Q, E, H, I, L, K, M, F, P, S, T, Y or V
<220> FEATURE:
<221> NAME/KEY: misc_feature
<222> LOCATION: (4)..(4)
<223> OTHER INFORMATION: Xaa is an amino acid selected from P and T

<400> SEQUENCE: 1

Phe Xaa Asp Xaa Gly Leu
1               5

<210> SEQ ID NO 2
<211> LENGTH: 236
<212> TYPE: PRT
<213> ORGANISM: Arthrobacter crystallopoietes

<400> SEQUENCE: 2

Met Arg Ile Leu Val Ile Asn Pro Asn Ser Ser Ala Leu Thr Glu
1               5                   10                  15

Ser Val Ala Asp Ala Ala Gln Gln Val Val Ala Thr Gly Thr Ile Ile
                20                  25                  30

Ser Ala Ile Asn Pro Ser Arg Gly Pro Ala Val Ile Glu Gly Ser Phe
            35                  40                  45

Asp Glu Ala Leu Ala Thr Phe His Leu Ile Glu Glu Val Glu Arg Ala
    50                  55                  60

Glu Arg Glu Asn Pro Pro Asp Ala Tyr Val Ile Ala Cys Phe Gly Asp
65                  70                  75                  80

Pro Gly Leu Asp Ala Val Lys Glu Leu Thr Asp Arg Pro Val Val Gly
                85                  90                  95

Val Ala Glu Ala Ala Ile His Met Ser Ser Phe Val Ala Ala Thr Phe
            100                 105                 110

Ser Ile Val Ser Ile Leu Pro Arg Val Arg Lys His Leu His Glu Leu
        115                 120                 125
```

```
Val Arg Gln Ala Gly Ala Thr Asn Arg Leu Ala Ser Ile Lys Leu Pro
    130                 135                 140

Asn Leu Gly Val Met Ala Phe His Glu Asp Glu His Ala Ala Leu Glu
145                 150                 155                 160

Thr Leu Lys Gln Ala Ala Lys Glu Ala Val Gln Glu Asp Gly Ala Glu
                165                 170                 175

Ser Ile Val Leu Gly Cys Ala Gly Met Val Gly Phe Ala Arg Gln Leu
                180                 185                 190

Ser Asp Glu Leu Gly Val Pro Val Ile Asp Pro Val Glu Ala Ala Cys
            195                 200                 205

Arg Val Ala Glu Ser Leu Val Ala Leu Gly Tyr Gln Thr Ser Lys Ala
    210                 215                 220

Asn Ser Tyr Gln Lys Pro Thr Glu Lys Gln Tyr Leu
225                 230                 235
```

<210> SEQ ID NO 3
<211> LENGTH: 711
<212> TYPE: DNA
<213> ORGANISM: Artificial sequence
<220> FEATURE:
<223> OTHER INFORMATION: mutated hydantoin racemase sequence of
      Arthrobacter crystallopoietes

<400> SEQUENCE: 3

```
atgagaatcc tcgtgatcaa ccccaacagt tccagcgccc ttactgaatc ggttgcggac    60
gcagcacaac aagttgtcgc gaccggcacc ataatttctg ccatcaaccc ctccagagga   120
cccgccgtca ttgaaggcag cttttgacgaa gcactggcca cgttccatct cattgaagag   180
gtggagcgcg ctgagcggga aaacccgccc gacgcctacg tcatcgcatg tttcagggat   240
ccgggacttg acgcggtcaa ggagctgact gacaggccag tggtaggagt tgccgaagct   300
gcaatccaca tgtcttcatt cgtcgcggcc accttctcca ttgtcagcat cctcccgagg   360
gtcaggaaac atctgcacga actggtacgg caagcggggg cgacgaatcg cctcgcctcc   420
atcaagctcc caaatctggg ggtgatggcc ttccatgagg acgaacatgc cgcactggag   480
acgctcaaac aagccgccaa ggaggcggtc caggaggacg gcgccgagtc gatagtgctc   540
ggatgcgccg gcatggtggg gtttgcgcgt caactgagcg acgaactcgg cgtccctgtc   600
atcgaccccg tcgaggcagc ttgccgcgtg gccgagagtt tggtcgctct gggctaccag   660
accagcaaag cgaactcgta tcaaaaaccg acagagaagc agtacctcta g           711
```

<210> SEQ ID NO 4
<211> LENGTH: 236
<212> TYPE: PRT
<213> ORGANISM: Artificial sequence
<220> FEATURE:
<223> OTHER INFORMATION: mutated hydantoin racemase sequence of
      Arthrobacter crystallopoietes

<400> SEQUENCE: 4

```
Met Arg Ile Leu Val Ile Asn Pro Asn Ser Ser Ala Leu Thr Glu
1               5                   10                  15

Ser Val Ala Asp Ala Ala Gln Gln Val Val Ala Thr Gly Thr Ile Ile
                20                  25                  30

Ser Ala Ile Asn Pro Ser Arg Gly Pro Ala Val Ile Glu Gly Ser Phe
            35                  40                  45

Asp Glu Ala Leu Ala Thr Phe His Leu Ile Glu Glu Val Glu Arg Ala
50                  55                  60
```

-continued

```
Glu Arg Glu Asn Pro Pro Asp Ala Tyr Val Ile Ala Cys Phe Arg Asp
 65                  70                  75                  80

Pro Gly Leu Asp Ala Val Lys Glu Leu Thr Asp Arg Pro Val Val Gly
                 85                  90                  95

Val Ala Glu Ala Ala Ile His Met Ser Ser Phe Val Ala Ala Thr Phe
            100                 105                 110

Ser Ile Val Ser Ile Leu Pro Arg Val Arg Lys His Leu His Glu Leu
        115                 120                 125

Val Arg Gln Ala Gly Ala Thr Asn Arg Leu Ala Ser Ile Lys Leu Pro
130                 135                 140

Asn Leu Gly Val Met Ala Phe His Glu Asp Glu His Ala Ala Leu Glu
145                 150                 155                 160

Thr Leu Lys Gln Ala Ala Lys Glu Ala Val Gln Glu Asp Gly Ala Glu
                165                 170                 175

Ser Ile Val Leu Gly Cys Ala Gly Met Val Gly Phe Ala Arg Gln Leu
            180                 185                 190

Ser Asp Glu Leu Gly Val Pro Val Ile Asp Pro Val Glu Ala Ala Cys
        195                 200                 205

Arg Val Ala Glu Ser Leu Val Ala Leu Gly Tyr Gln Thr Ser Lys Ala
    210                 215                 220

Asn Ser Tyr Gln Lys Pro Thr Glu Lys Gln Tyr Leu
225                 230                 235
```

<210> SEQ ID NO 5
<211> LENGTH: 711
<212> TYPE: DNA
<213> ORGANISM: Artificial sequence
<220> FEATURE:
<223> OTHER INFORMATION: mutated hydantoin racemase sequence of
      Arthrobacter crystallopoietes

<400> SEQUENCE: 5

```
atgagaatcc tcgtgatcaa ccccaacagt tccagcgccc ttactgaatc ggttgcggac     60
gcagcacaac aagttgtcgc gaccggcacc ataatttctg ccatcaaccc ctccagagga    120
cccgccgtca ttgaaggcag cttttgacgaa gcactggcca cgttccatct cattgaagag    180
gtggagcgcg ctgagcggga aaacccgccc gacgcctacg tcatcgcatg tttcgaggat    240
ccgggacttg acgcggtcaa ggagctgact gacaggccag tggtaggagt tgccgaagct    300
gcaatccaca tgtcttcatt cgtcgcggcc accttctcca ttgtcagcat cctcccgagg    360
gtcaggaaac atctgcacga actggtacgg caagcggggg cgacgaatcg cctcgcctcc    420
atcaagctcc caaatctggg ggtgatggcc ttccatgagg acgaacatgc cgcactggag    480
acgctcaaac aagccgccaa ggaggcggtc caggaggacg gcgccgagtc gatagtgctc    540
ggatgcgccg gcatggtggg gtttgcgcgt caactgagcg acgaactcgg cgtccctgtc    600
atcgaccccg tcgaggcagc ttgccgcgtg gccgagagtt tggtcgctct gggctaccag    660
accagcaaag cgaactcgta tcaaaaaccg acagagaagc agtacctcta g            711
```

<210> SEQ ID NO 6
<211> LENGTH: 236
<212> TYPE: PRT
<213> ORGANISM: Artificial sequence
<220> FEATURE:
<223> OTHER INFORMATION: mutated hydantoin racemase sequence of
      Arthrobacter crystallopoietes

<400> SEQUENCE: 6

```
Met Arg Ile Leu Val Ile Asn Pro Asn Ser Ser Ala Leu Thr Glu
1               5                   10                  15

Ser Val Ala Asp Ala Ala Gln Gln Val Val Ala Thr Gly Thr Ile Ile
            20                  25                  30

Ser Ala Ile Asn Pro Ser Arg Gly Pro Ala Val Ile Glu Gly Ser Phe
            35                  40                  45

Asp Glu Ala Leu Ala Thr Phe His Leu Ile Glu Glu Val Glu Arg Ala
    50                  55                  60

Glu Arg Glu Asn Pro Pro Asp Ala Tyr Val Ile Ala Cys Phe Glu Asp
65                  70                  75                  80

Pro Gly Leu Asp Ala Val Lys Glu Leu Thr Asp Arg Pro Val Val Gly
                85                  90                  95

Val Ala Glu Ala Ala Ile His Met Ser Ser Phe Val Ala Thr Phe
                100                 105                 110

Ser Ile Val Ser Ile Leu Pro Arg Val Arg Lys His Leu His Glu Leu
            115                 120                 125

Val Arg Gln Ala Gly Ala Thr Asn Arg Leu Ala Ser Ile Lys Leu Pro
    130                 135                 140

Asn Leu Gly Val Met Ala Phe His Glu Asp His Ala Ala Leu Glu
145                 150                 155                 160

Thr Leu Lys Gln Ala Ala Lys Glu Ala Val Gln Glu Asp Gly Ala Glu
                165                 170                 175

Ser Ile Val Leu Gly Cys Ala Gly Met Val Gly Phe Ala Arg Gln Leu
            180                 185                 190

Ser Asp Glu Leu Gly Val Pro Val Ile Asp Pro Val Glu Ala Ala Cys
    195                 200                 205

Arg Val Ala Glu Ser Leu Val Ala Leu Gly Tyr Gln Thr Ser Lys Ala
    210                 215                 220

Asn Ser Tyr Gln Lys Pro Thr Glu Lys Gln Tyr Leu
225                 230                 235
```

<210> SEQ ID NO 7
<211> LENGTH: 711
<212> TYPE: DNA
<213> ORGANISM: Artificial sequence
<220> FEATURE:
<223> OTHER INFORMATION: mutated hydantoin racemase sequence of
    Arthrobacter crystallopoietes

<400> SEQUENCE: 7

| | |
|---|---|
| atgagaatcc tcgtgatcaa ccccaacagt tccagcgccc ttactgaatc ggttgcggac | 60 |
| gcagcacaac aagttgtcgc gaccggcacc ataatttctg ccatcaaccc ctccagagga | 120 |
| cccgccgtca ttgaaggcag cttttgacgaa gcactggcca cgttccatct cattgaagag | 180 |
| gtggagcgcg ctgagcggga aaacccgccc gacgcctacg tcatcgcatg tttccaggat | 240 |
| ccgggacttg acgcggtcaa ggagctgact gacaggccag tggtaggagt tgccgaagct | 300 |
| gcaatccaca tgtcttcatt cgtcgcggcc accttctcca ttgtcagcat cctcccgagg | 360 |
| gtcaggaaac atctgcacga actggtacgg caagcggggg cgacgaatcg cctcgcctcc | 420 |
| atcaagctcc caaatctggg ggtgatggcc ttccatgagg acgaacatgc cgcactggag | 480 |
| acgctcaaac aagccgccaa ggaggcggtc caggaggacg gcgccgagtc gatagtgctc | 540 |
| ggatgcgccg gcatggtggg gtttgcgcgt caactgagcg acgaactcgg cgtccctgtc | 600 |
| atcgacccccg tcgaggcagc ttgccgcgtg gccgagagtt tggtcgctct gggctaccag | 660 |
| accagcaaag cgaactcgta tcaaaaaccg acagagaagc agtacctcta g | 711 |

<210> SEQ ID NO 8
<211> LENGTH: 236
<212> TYPE: PRT
<213> ORGANISM: Artificial sequence
<220> FEATURE:
<223> OTHER INFORMATION: mutated hydantoin racemase sequence of
      Arthrobacter crystallopoietes

<400> SEQUENCE: 8

Met Arg Ile Leu Val Ile Asn Pro Asn Ser Ser Ala Leu Thr Glu
1               5                   10                  15

Ser Val Ala Asp Ala Ala Gln Gln Val Val Ala Thr Gly Thr Ile Ile
                20                  25                  30

Ser Ala Ile Asn Pro Ser Arg Gly Pro Ala Val Ile Glu Gly Ser Phe
                35                  40                  45

Asp Glu Ala Leu Ala Thr Phe His Leu Ile Glu Glu Val Glu Arg Ala
                50                  55                  60

Glu Arg Glu Asn Pro Pro Asp Ala Tyr Val Ile Ala Cys Phe Gln Asp
65                  70                  75                  80

Pro Gly Leu Asp Ala Val Lys Glu Leu Thr Asp Arg Pro Val Val Gly
                85                  90                  95

Val Ala Glu Ala Ala Ile His Met Ser Ser Phe Val Ala Ala Thr Phe
                100                 105                 110

Ser Ile Val Ser Ile Leu Pro Arg Val Arg Lys His Leu His Glu Leu
                115                 120                 125

Val Arg Gln Ala Gly Ala Thr Asn Arg Leu Ala Ser Ile Lys Leu Pro
                130                 135                 140

Asn Leu Gly Val Met Ala Phe His Glu Asp Glu His Ala Ala Leu Glu
145                 150                 155                 160

Thr Leu Lys Gln Ala Ala Lys Glu Ala Val Gln Glu Asp Gly Ala Glu
                165                 170                 175

Ser Ile Val Leu Gly Cys Ala Gly Met Val Gly Phe Ala Arg Gln Leu
                180                 185                 190

Ser Asp Glu Leu Gly Val Pro Val Ile Asp Pro Val Glu Ala Ala Cys
                195                 200                 205

Arg Val Ala Glu Ser Leu Val Ala Leu Gly Tyr Gln Thr Ser Lys Ala
210                 215                 220

Asn Ser Tyr Gln Lys Pro Thr Glu Lys Gln Tyr Leu
225                 230                 235

<210> SEQ ID NO 9
<211> LENGTH: 711
<212> TYPE: DNA
<213> ORGANISM: Artificial sequence
<220> FEATURE:
<223> OTHER INFORMATION: mutated hydantoin racemase sequence of
      Arthrobacter crystallopoietes

<400> SEQUENCE: 9
atgagaatcc tcgtgatcaa ccccaacagt tccagcgccc ttactgaatc ggttgcggac      60
gcagcacaac aagttgtcgc gaccggcacc ataatttctg ccatcaaccc ctccagagga     120
cccgccgtca ttgaaggcag ctttgacgaa gcactggcca cgttccatct cattgaagag     180
gtggagcgcg ctgagcggga aaacccgccc gacgcctacg tcatcgcatg tttcttggat     240
ccgggacttg acgcggtcaa ggagctgact gacaggccag tggtaggagt tgccgaagct     300
gcaatccaca tgtcttcatt cgtcgcggcc accttctcca ttgtcagcat cctcccgagg     360

```
gtcaggaaac atctgcacga actggtacgg caagcggggg cgacgaatcg cctcgcctcc      420
atcaagctcc caaatctggg ggtgatggcc ttccatgagg acgaacatgc cgcactggag      480
acgctcaaac aagccgccaa ggaggcggtc caggaggacg cgccgagtc gatagtgctc       540 ggatgcgccg gcatggtggg gtttgcgcgt caactgagcg acgaactcgg cgtccctgtc      600
atcgaccccg tcgaggcagc ttgccgcgtg gccgagagtt tggtcgctct gggctaccag      660
accagcaaag cgaactcgta tcaaaaaccg acagagaagc agtacctcta g              711
```

```
<210> SEQ ID NO 10
<211> LENGTH: 236
<212> TYPE: PRT
<213> ORGANISM: Artificial sequence
<220> FEATURE:
<223> OTHER INFORMATION: mutated hydantoin racemase sequence of
      Arthrobacter crystallopoietes

<400> SEQUENCE: 10
```

```
Met Arg Ile Leu Val Ile Asn Pro Asn Ser Ser Ala Leu Thr Glu
1               5                   10                  15

Ser Val Ala Asp Ala Ala Gln Gln Val Val Ala Thr Gly Thr Ile Ile
            20                  25                  30

Ser Ala Ile Asn Pro Ser Arg Gly Pro Ala Val Ile Glu Gly Ser Phe
        35                  40                  45

Asp Glu Ala Leu Ala Thr Phe His Leu Ile Glu Glu Val Glu Arg Ala
    50                  55                  60

Glu Arg Glu Asn Pro Pro Asp Ala Tyr Val Ile Ala Cys Phe Leu Asp
65                  70                  75                  80

Pro Gly Leu Asp Ala Val Lys Glu Leu Thr Asp Arg Pro Val Val Gly
                85                  90                  95

Val Ala Glu Ala Ala Ile His Met Ser Ser Phe Val Ala Ala Thr Phe
            100                 105                 110

Ser Ile Val Ser Ile Leu Pro Arg Val Arg Lys His Leu His Glu Leu
        115                 120                 125

Val Arg Gln Ala Gly Ala Thr Asn Arg Leu Ala Ser Ile Lys Leu Pro
    130                 135                 140

Asn Leu Gly Val Met Ala Phe His Glu Asp His Ala Ala Leu Glu
145                 150                 155                 160

Thr Leu Lys Gln Ala Ala Lys Glu Ala Val Gln Glu Asp Gly Ala Glu
                165                 170                 175

Ser Ile Val Leu Gly Cys Ala Gly Met Val Gly Phe Ala Arg Gln Leu
            180                 185                 190

Ser Asp Glu Leu Gly Val Pro Val Ile Asp Pro Val Glu Ala Ala Cys
        195                 200                 205

Arg Val Ala Glu Ser Leu Val Ala Leu Gly Tyr Gln Thr Ser Lys Ala
    210                 215                 220

Asn Ser Tyr Gln Lys Pro Thr Glu Lys Gln Tyr Leu
225                 230                 235
```

```
<210> SEQ ID NO 11
<211> LENGTH: 25
<212> TYPE: DNA
<213> ORGANISM: Artificial sequence
<220> FEATURE:
<223> OTHER INFORMATION: PCR plasmid for ampifying plasmids containing a
      sequence encoding hydantoin racemase of Arthrobacter
      crystallopoietes
```

-continued

<400> SEQUENCE: 11
gccgcaagga atggtgcatg catcg                                         25

<210> SEQ ID NO 12
<211> LENGTH: 30
<212> TYPE: DNA
<213> ORGANISM: Artificial sequence
<220> FEATURE:
<223> OTHER INFORMATION: PCR plasmid for ampifying plasmids containg a
      sequence encoding hydantoin racemase of Arthrobacter
      crystallopoietes

<400> SEQUENCE: 12
ggtcaggtgg gtccaccgcg ctactgccgc                                    30

<210> SEQ ID NO 13
<211> LENGTH: 5777
<212> TYPE: DNA
<213> ORGANISM: Artificial sequence
<220> FEATURE:
<223> OTHER INFORMATION: plasmid containing sequence encoding hydantoin
      racemase of Arthrobacter crystallopoietes

<400> SEQUENCE: 13
aattcttaag aaggagatat acatatgaga atcctcgtga tcaaccccaa cagttccagc      60
gcccttactg aatcggttgc ggacgcagca caacaagttg tcgcgaccgg caccataatt    120
tctgccatca acccctccag aggacccgcc gtcattgaag gcagctttga cgaagcactg    180
gccacgttcc atctcattga agaggtggag cgcgctgagc gggaaaaccc gcccgacgcc    240
tacgtcatcg catgtttcgg ggatccggga cttgacgcgg tcaaggagct gactgacagg    300
ccagtggtag gagttgccga agctgcaatc cacatgtctt cattcgtcgc ggccaccttc    360
tccattgtca gcatcctccc gagggtcagg aaacatctgc acgaactggt acggcaagcg    420
ggggcgacga atcgcctcgc ctccatcaag ctcccaaatc tggggtgat ggccttccat     480 gaggacgaac atgccgcact ggagacgctc aaacaagccg ccaaggaggc ggtccaggag    540
gacggcgccg agtcgatagt gctcggatgc gccggcatgg tggggtttgc gcgtcaactg    600
agcgacgaac tcggcgtccc tgtcatcgac cccgtcgagg cagcttgccg cgtggccgag    660
agtttggtcg ctctgggcta ccagaccagc aaagcgaact cgtatcaaaa accgacagag    720
aagcagtacc tctagctgca gccaagcttc tgttttggcg gatgagagaa gattttcagc    780
ctgatacaga ttaaatcaga acgcagaagc ggtctgataa acagaatttg cctggcggc     840 agtagcgcgg tggtcccacc tgaccccatg ccgaactcag aagtgaaacg ccgtagcgcc    900
gatggtagtg tggggtctcc ccatgcgaga gtagggaact gccaggcatc aaataaaacg    960
aaaggctcag tcgaaagact gggcctttcg ttttatctgt tgtttgtcgg tgaacgctct   1020
cctgagtagg acaaatccgc cgggagcgga tttgaacgtt gcgaagcaac ggcccggagg   1080
gtggcgggca ggacgcccgc cataaactgc caggcatcaa attaagcaga aggccatcct   1140
gacggatggc cttttttgcgt ttctacaaac tcttttgttt attttttctaa atacattcaa   1200 atatgtatcc gctcatgaga caataaccct gataaatgct tcaataatat cgtccattcc   1260
gacagcatcg ccagtcacta tggcgtgctg ctagcgctat atgcgttgat gcaatttcta   1320
tgcgcacccg ttctcggagc actgtccgac cgctttggcc gccgccagt cctgctcgct    1380 tcgctacttg gagccactat cgactacgcg atcatggcga ccacaccgt cctgtggatc    1440 ctctacgccg gacgcatcgt ggccggcatc accggcgcca caggtgcggt tgctggcgcc    1500

-continued

```
tatatcgccg acatcaccga tggggaagat cgggctcgcc acttcgggct catgagcgct    1560
tgtttcggcg tgggtatggt ggcaggcccc gtggccgggg gactgttggg cgccatctcc    1620
ttgcatgcac cattccttgc ggcggcggtg ctcaacggcc tcaacctact actgggctgc    1680
ttcctaatgc aggagtcgca taagggagag cgtcgaccga tgcccttgag agccttcaac    1740
ccagtcagct ccttccggtg ggcgcggggc atgactatcg tcgccgcact tatgactgtc    1800
ttctttatca tgcaactcgt aggacaggtg ccggcagcgc tctgggtcat tttcggcgag    1860
gaccgctttc gctggagcgc gacgatgatc ggcctgtcgc ttgcggtatt cggaatcttg    1920
cacgccctcg ctcaagcctt cgtcactggt cccgccacca acgtttcgg cgagaagcag    1980
gccattatcg ccggcatggc ggccgacgcg ctgggctacg tcttgctggc gttcgcgacg    2040
cgaggctgga tggccttccc cattatgatt cttctcgctt ccggcggcat cgggatgccc    2100
gcgttgcagg ccatgctgtc caggcaggta gatgacgacc atcagggaca gcttcaagga    2160
tcgctcgcgg ctcttaccag cctaacttcg atcactggac cgctgatcgt cacggcgatt    2220
tatgccgcct cggcgagcac atggaacggg ttggcatgga ttgtaggcgc cgccctatac    2280
cttgtctgcc tccccgcgtt gcgtcgcggt gcatggagcc gggccacctc gacctgaatg    2340
gaagccggcg gcacctcgct aacggattca ccactccaag aattggagcc aatcaattct    2400
tgcggagaac tgtgaatgcg caaaccaacc cttggcagaa catatccatc gcgtccgcca    2460
tctccagcag ccgcacgcgg cgcatctcgg gcagcgttgg gtcctggcca cgggtgcgca    2520
tgatcgtgct cctgtcgttg aggacccggc taggctggcg gggttgcctt actggttagc    2580
agaatgaatc accgatacgc gagcgaacgt gaagcgactg ctgctgcaaa acgtctgcga    2640
cctgagcaac aacatgaatg gtcttcggtt tccgtgtttc gtaaagtctg gaaacgcgga    2700
agtcccctac gtgctgctga agttgcccgc aacagagagt ggaaccaacc ggtgatacca    2760
cgatactatg actgagagtc aacgccatga gcggcctcat ttcttattct gagttacaac    2820
agtccgcacc gctgtccggt agctccttcc ggtgggcgcg gggcatgact atcgtcgccg    2880
cacttatgac tgtcttcttt atcatgcaac tcgtaggaca ggtgccggca gcgcccaaca    2940
gtcccccggc cacggggcct gccaccatac ccacgccgaa acaagcgccc tgcaccatta    3000
tgttccggat ctgcatcgca ggatgctgct ggctaccctg tggaacacct acatctgtat    3060
taacgaagcg ctaaccgttt ttatcaggct ctgggaggca gaataaatga tcatatcgtc    3120
aattattacc tccacgggga gagcctgagc aaactggcct caggcatttg agaagcacac    3180
ggtcacactg cttccggtag tcaataaacc ggtaaaccag caatagacat aagcggctat    3240
ttaacgaccc tgccctgaac cgacgaccgg gtcgaatttg ctttcgaatt tctgccattc    3300
atccgcttat tatcacttat tcaggcgtag caccaggcgt ttaagggcac caataactgc    3360
cttaaaaaaa ttacgccccg ccctgccact catcgcagta ctgttgtaat tcattaagca    3420
ttctgccgac atggaagcca tcacagacg catgatgaac ctgaatcgcc agcggcatca    3480
gcaccttgtc gccttgcgta taatatttgc ccatggtgaa aacgggggcg aagaagttgt    3540
ccatattggc cacgtttaaa tcaaaactgg tgaaactcac ccagggattg gctgagacga    3600
aaaacatatt ctcaataaac cctttaggga ataggccag gttttcaccg taacacgcca    3660
catcttgcga atatatgtgt agaaactgcc ggaaatcgtc gtggtattca ctccagagcg    3720
atgaaaacgt ttcagtttgc tcatggaaaa cggtgtaaca agggtgaaca ctatcccata    3780
tcaccagctc accgtctttc attgccatac gaattccgga tgagcattca tcaggcgggc    3840
aagaatgtga ataaaggccg gataaaactt gtgcttattt ttctttacgg tctttaaaaa    3900
```

```
ggccgtaata tccagctgaa cggtctggtt ataggtacat tgagcaactg actgaaatgc    3960
ctcaaaatgt tctttacgat gccattggga tatatcaacg gtggtatatc cagtgatttt    4020
tttctccatt ttagcttcct tagctcctga aaatctcgat aactcaaaaa atacgcccgg    4080
tagtgatctt atttcattat ggtgaaagtt ggaacctctt acgtgccgat caacgtctca    4140
ttttcgccaa aagttggccc agggcttccc ggtatcaaca gggacaccag gatttattta    4200
ttctgcgaag tgatcttccg tcacaggtat ttattcggcg caaagtgcgt cgggtgatgc    4260
tgccaactta ctgatttagt gtatgatggt gttttttgagg tgctccagtg gcttctgttt    4320
ctatcagctg tccctcctgt tcagctactg acggggtggt gcgtaacggc aaaagcaccg    4380
ccggacatca gcgctagcgg agtgtatact ggcttactat gttggcactg atgagggtgt    4440
cagtgaagtg cttcatgtgg caggagaaaa aaggctgcac cggtgcgtca gcagaatatg    4500
tgatacagga tatattccgc ttcctcgctc actgactcgc tacgctcggt cgttcgactg    4560
cggcgagcgg aaatggctta cgaacggggc ggagatttcc tggaagatgc caggaagata    4620
cttaacaggg aagtgagagg gccgcggcaa agccgttttt ccataggctc cgccccctg    4680 acaagcatca cgaaatctga cgctcaaatc agtggtggcg aaacccgaca ggactataaa    4740
gataccaggc gtttccctg gcggctccct cgtgcgctct cctgttcctg cctttcggtt    4800
taccggtgtc attccgctgt tatggccgcg tttgtctcat tccacgcctg acactcagtt    4860
ccgggtaggc agttcgctcc aagctggact gtatgcacga accccccgtt cagtccgacc    4920
gctgcgcctt atccggtaac tatcgtcttg agtccaaccc ggaaagacat gcaaaagcac    4980
cactggcagc agccactggt aattgattta gaggagttag tcttgaagtc atgcgccggt    5040
taaggctaaa ctgaaaggac aagttttggt gactgcgctc ctccaagcca gttacctcgg    5100
ttcaaagagt tggtagctca gagaaccttc gaaaaaccgc cctgcaaggc ggttttttcg    5160
ttttcagagc aagagattac gcgcagacca aacgatctc aagaagatca tcttattaat    5220
cagataaaat atttcaagat ttcagtgcaa tttatctctt caaatgtagc acctgaagtc    5280
agccccatac gatataagtt gtaattctca tgtttgacag cttatcatcg ataagcttta    5340
atgcggtagt ttatcacagt taaattgcta acgcagtcag gcaccgtgta tgaaatctaa    5400
caatgcgctc atcgtcatcc tcggcaccgt caccctggat gctgtaggca taggcttggt    5460
tatgccggta ctgccgggcc tcttgcggga ttagtcatgc cccgcgccca ccggaaggag    5520
ctgactgggt tgaaggctct caagggcatc ggtcgacgct ctcccttatg cgactcctgc    5580
attaggaagc agcccagtag taggttgagg ccgttgagca ccgccgccgc aaggaatggt    5640
gcatgcatcg atcaccacaa ttcagcaaat tgtgaacatc atcacgttca tctttccctg    5700
gttgccaatg gcccattttc ctgtcagtaa cgagaaggtc gcgaattcag gcgcttttta    5760
gactggtcgt aatgaac                                                    5777
```

<210> SEQ ID NO 14
<211> LENGTH: 7175
<212> TYPE: DNA
<213> ORGANISM: Artificial sequence
<220> FEATURE:
<223> OTHER INFORMATION: plasmid containing sequence encoding hydantoin racemase of Arthrobacter crystallopoietes
<220> FEATURE:
<221> NAME/KEY: misc_feature
<222> LOCATION: (49)..(49)
<223> OTHER INFORMATION: n is a, c, g, or t

<400> SEQUENCE: 14

-continued

```
aattcttaag aaggagatat acatatgacc ctgcagaaag cgcaagcgna gcgcattgag      60
aaagagatct gggagctctc ccggttctcg gcggaaggcc ccggtgttac ccggctgacc     120
tacactccag agcatgccgc cgcgcgggaa acgctcattg cggctatgga agcggccgct     180
ttgagcgttc gtgaagacgc tctcgggaac atcatcggcc gacgtgaagg cactgatccg     240
cagctccctg cgatcgcggt cggttcacac ttcgattctg tccgaaacgg cgggatgttc     300
gatggcactg caggcgtggt gtgcgccctt gaggctgccc gggtgatgct ggagagcggc     360
tacgtgaatc ggcatccatt tgagttcatc gcgatcgtgg aggaggaagg ggcccgcttc     420
agcagtggca tgttgggcgg ccgggccatt gcaggtttgg tcgccgacag ggaactggac     480
tctttggttg atgaggatgg agtgtccgtt aggcaggcgg ctactgcctt cggcttgaag     540
ccgggcgaac tgcaggctgc agcccgctcc gcggcggacc tgcgtgcttt tatcgaacta     600
cacattgaac aaggaccgat cctcgagcag gagcaaatag agatcggagt tgtgacctcc     660
atcgttggcg ttcgcgcatt gcgggttgct gtcaaaggca gaagcgcaca cgccggcaca     720
accccccatgc acctgcgcca ggatgcgctg gtacccgccg ctctcatggt gcgggaggtc     780
aaccggttcg tcaacgagat cgccgatggc acagtggcta ccgttggcca cctcacagtg     840
gccccccggtg gcggcaacca ggtcccgggg gaggtggagt tcacactgga cctgcgttct     900
ccgcatgagg agtcgctccg ggtgttgatc aaccgcatct cggtcatggt cggcgaggtc     960
gcctcgcagg ccggtgtggc tgccgatgtg gatgaatttt tcaatctcag cccggtgcag    1020
ctggctccta ccatggtgga cgccgttcgc gaagcggcct cggccctgca gttcacgcac    1080
cgggatatca gcagtggggc gggccacgac tcgatgttca tcgcccaggt cacggacgtc    1140
ggaatggttt tcgttccaag ccgtgctggc cggagccacg ttcccgaaga atggaccgat    1200
ttcgatgacc ttcgcaaggg aactgaggtt gtcctccggg taatgaaggc acttgaccgg    1260
ggatcccatc atcatcatca tcattgactg cagccaagct tctgtttttgg cggatgagag    1320
aagattttca gcctgataca gattaaatca gaacgcagaa gcggtctgat aaaacagaat    1380
ttgcctggcg gcagtagcgc ggtggtccca cctgacccca tgccgaactc agaagtgaaa    1440
cgccgtagcg ccgatggtag tgtgggtct ccccatgcga gagtagggaa ctgccaggca    1500
tcaaataaaa cgaaaggctc agtcgaaaga ctgggccttt cgttttatct gttgtttgtc    1560
ggtgaacgct ctcctgagta ggacaaatcc gccgggagcg gatttgaacg ttgcgaagca    1620
acggcccgga gggtggcggg caggacgccc gccataaact gccaggcatc aaattaagca    1680
gaaggccatc ctgacggatg gcctttttgc gtttctacaa actcttttgt ttatttttct    1740
aaatacattc aaatatgtat ccgctcatga gacaataacc ctgataaatg cttcaataat    1800
attgaaaaag gaagagtatg agtattcaac atttccgtgt cgcccttatt ccctttttttg    1860
cggcattttg ccttcctgtt tttgctcacc cagaaacgct ggtgaaagta aaagatgctg    1920
aagatcagtt gggtgcacga gtgggttaca tcgaactgga tctcaacagc ggtaagatcc    1980
ttgagagttt cgccccgaa gaacgttttc caatgatgag cacttttaaa gttctgctat    2040
gtggcgcggt attatcccgt gttgacgccg ggcaagagca actcggtcgc cgcatacact    2100
attctcagaa tgacttggtt gagtactcac cagtcacaga aaagcatctt acggatggca    2160
tgacagtaag agaattatgc agtgctgcca taaccatgag tgataacact gcggccaact    2220
tacttctgac aacgatcgga ggaccgaagg agctaaccgc ttttttgcac aacatggggg    2280
atcatgtaac tcgccttgat cgttgggaac cggagctgaa tgaagccata ccaaacgacg    2340
```

-continued

```
agcgtgacac cacgatgcct gtagcaatgg caacaacgtt gcgcaaacta ttaactggcg    2400
aactacttac tctagcttcc cggcaacaat taatagactg gatggaggcg gataaagttg    2460
caggaccact tctgcgctcg gcccttccgg ctggctggtt tattgctgat aaatctggag    2520
ccggtgagcg tgggtctcgc ggtatcattg cagcactggg gccagatggt aagccctccc    2580
gtatcgtagt tatctacacg acggggagtc aggcaactat ggatgaacga atagacaga    2640
tcgctgagat aggtgcctca ctgattaagc attggtaact gtcagaccaa gtttactcat    2700
atatacttta gattgattta aaacttcatt tttaatttaa aaggatctag gtgaagatcc    2760
tttttgataa tctcatgacc aaaatccctt aacgtgagtt ttcgttccac tgagcgtcag    2820
accccgtaga aaagatcaaa ggatcttctt gagatccttt ttttctgcgc gtaatctgct    2880
gcttgcaaac aaaaaaacca ccgctaccag cggtggtttg tttgccggat caagagctac    2940
caactctttt tccgaaggta actggcttca gcagagcgca gataccaaat actgtccttc    3000
tagtgtagcc gtagttaggc caccacttca agaactctgt agcaccgcct acatacctcg    3060
ctctgctaat cctgttacca gtggctgctg ccagtggcga taagtcgtgt cttaccgggt    3120
tggactcaag acgatagtta ccggataagg cgcagcggtc gggctgaacg ggggggttcgt   3180
gcacacagcc cagcttggag cgaacgacct acaccgaact gagatacta cagcgtgagc    3240
tatgagaaag cgccacgctt cccgaaggga gaaaggcgga caggtatccg gtaagcggca    3300
gggtcggaac aggagagcgc acgagggagc ttccaggggg aaacgcctgg tatctttata    3360
gtcctgtcgg gtttcgccac ctctgacttg agcgtcgatt tttgtgatgc tcgtcagggg    3420
ggcggagcct atggaaaaac gccagcaacg cggccttttt acggttcctg gccttttgct    3480
ggccttttgc tcacatgttc tttcctgcgt tatcccctga ttctgtggat aaccgtatta    3540
ccgcctttga gtgagctgat accgctcgcc gcagccgaac gaccgagcgc agcgagtcag    3600
tgagcgagga gcggaagag cgcctgatgc ggtattttct ccttacgcat ctgtgcggta    3660
tttcacaccg catatatggt gcactctcag tacaatctgc tctgatgccg catagttaag    3720
ccagtataca ctccgctatc gctacgtgac tgggtcatgg ctgcgccccg acacccgcca    3780
acaccgctg acgcgccctg acgggcttgt ctgctcccgg catccgctta cagacaagct    3840
gtgaccgtct ccgggagctg catgtgtcag aggttttcac cgtcatcacc gaaacgcgcg    3900
aggcagctgc ggtaaagctc atcagcgtgg tcgtgaagcg attcacagat gtctgcctgt    3960
tcatccgcgt ccagctcgtt gagtttctcc agaagcgtta atgtctggct tctgataaag    4020
cgggccatgt taagggcggt ttttttcctgt ttggtcactt gatgcctccg tgtaaggggg    4080
aatttctgtt catggggta atgataccga tgaaacgaga aggatgctca cgatacggg     4140
ttactgatga tgaacatgcc cggttactgg aacgttgtga ggtaaacaa ctggcggtat    4200
ggatgcggcg ggaccagaga aaatcactc agggtcaatg ccagcgcttc gttaatacag    4260
atgtaggtgt tccacagggt agccagcagc atcctgcgat gcagatccgg aacataatgg    4320
tgcagggcgc tgacttccgc gtttccagac tttacgaaac acggaaaccg aagaccattc    4380
atgttgttgc tcaggtcgca gacgttttgc agcagcagtc gcttcacgtt cgctcgcgta    4440
tcggtgattc attctgctaa ccagtaaggc aaccccgcca gcctagccgg gtcctcaacg    4500
acaggagcac gatcatgcgc acccgtggcc aggacccaac gctgcccgag atgcgccgcg    4560
tgcggctgct ggagatggcg gacgcgatgg atatgttctg ccaagggttg gtttgcgcat    4620
tcacagttct ccgcaagaat tgattggctc caattcttgg agtggtgaat ccgttagcga    4680
ggtgccgccg gcttccattc aggtcgaggt ggcccggctc catgcaccgc gacgcaacgc    4740
```

```
ggggaggcag acaaggtata gggcggcgcc tacaatccat gccaacccgt tccatgtgct   4800
cgccgaggcg gcataaatcg ccgtgacgat cagcggtcca gtgatcgaag ttaggctggt   4860
aagagccgcg agcgatcctt gaagctgtcc ctgatggtcg tcatctacct gcctggacag   4920
catggcctgc aacgcgggca tcccgatgcc gccggaagcg agaagaatca taatggggaa   4980
ggccatccag cctcgcgtcg cgaacgccag caagacgtag cccagcgcgt cggccgccat   5040
gccggcgata atggcctgct tctcgccgaa acgtttggtg gcgggaccag tgacgaaggc   5100
ttgagcgagg gcgtgcaaga ttccgaatac cgcaagcgac aggccgatca tcgtcgcgct   5160
ccagcgaaag cggtcctcgc cgaaaatgac ccagagcgct gccggcacct gtcctacgag   5220
ttgcatgata aagaagacag tcataagtgc ggcgacgata gtcatgcccc gcgcccaccg   5280
gaaggagctg actgggttga aggctctcaa gggcatcggt cgacgctctc ccttatgcga   5340
ctcctgcatt aggaagcagc ccagtagtag gttgaggccg ttgagcaccg ccgccgcaag   5400
gaatggtgca tgcatcgatc accacaattc agcaaattgt gaacatcatc acgttcatct   5460
ttccctggtt gccaatggcc cattttcctg tcagtaacga aaggtcgcg aattcaggcg    5520
cttttttagac tggtcgtaat gaacaattct taagaaggag atatacatat gtttgacgta   5580
atagttaaga actgccgtat ggtgtccagc gacggaatca ccgaggcaga cattctggtg   5640
aaagacggca aagtcgccgc aatcagctcg acacaagtg atgttgaggc gagccgaacc    5700
attgacgcgg gtggcaagtt cgtgatgccg ggcgtggtcg atgaacatgt gcatatcatc   5760
gacatggatc tgaagaaccg gtatggccgc ttcgaactcg attccgagtc tgcggccgtg   5820
ggaggcatca ccaccatctt tgagatgccg tttaccttcc cgcccaccac cactttggac   5880
gccttcctcg aaaagaagaa gcaggcgggg cagcggttga agttgactt cgcgctctat    5940
ggcggtggag tgccgggaaa cctgcccgag atccgcaaaa tgcacgacgc cggcgcagtg   6000
ggcttcaagt caatgatggc agcctcagtt ccgggcatgt tcgacgccgt cagcgacggc   6060
gaactgttcg aaatcttcca ggagatcgca gcctgtggtt cagtcgccgt ggtccatgcc   6120
gagaatgaaa cgatcattca agcgctccag aagcagatca aagccgctgg tcgcaaggac   6180
atggccgcct acgaggcatc ccaaccagtt ttccaggaga acgaggccat tcagcgtgcg   6240
ttactactgc agaagaagc cggctgtcga ctgattgtgc ttcacgtgag caaccctgac    6300
ggggtcgagc tgatacatcg ggcgcaatcc gagggccagg acgtccactg cgagtcgggt   6360
ccgcagtatc tgaatatcac cacgacgac gccgaacgaa tcggaccgta tatgaaggtc    6420
gcgccgcccg tccgctcagc cgagatgaac gtcagattat gggaacaact tgagaacggg   6480
ctcatcgaca cccttgggtc agaccacggc ggacatcctg tcgaggacaa agaacccggc   6540
tggaaggacg tgtggaaagc cggcaacggt gcgctgggcc ttgagacatc cctgcctatg   6600
atgctgacca acggagtgaa taaaggcagg ctatccttgg aacgcctcgt cgaggtgatg   6660
tgcgagaaac ctgcgaagct cttttggcatc tatccgcaga agggcacgct acaggttggt   6720
tccgacgccg atctgctcat cctcgatctg gatattgaca ccaaagtgga tgcctcgcag   6780
ttccgatccc tgcataagta cagcccgttc gacgggatgc ccgtcacggg tgcaccggtt   6840
ctgacgatgg tgcgcggaac ggtggtggca gagaagggag aagttctggt cgagcaggga   6900
ttcggccagt tcgtcacccg tcacgactac gaggcgtcga agtgaggatc tcgacgctct   6960
cccttatgcg actcctgcat taggaagcag cccagtagta ggttgaggcc gttgagcacc   7020
gccgccgcaa ggaatggtgc atgcatcgat caccacaatt cagcaaattg tgaacatcat   7080
```

```
cacgttcatc tttccctggt tgccaatggc ccattttcct gtcagtaacg agaaggtcgc    7140
gaattcaggc gcttttttaga ctggtcgtaa tgaac                              7175

<210> SEQ ID NO 15
<211> LENGTH: 5989
<212> TYPE: DNA
<213> ORGANISM: Artificial sequence
<220> FEATURE:
<223> OTHER INFORMATION: plasmid containing sequence encoding hydantoin
      racemase of Arthrobacter crystallopoietes

<400> SEQUENCE: 15
aattcttaag aaggagatat acatatggat gcaaagctac tggttggcgg cactattgtt      60
tcctcgaccg gcaaaatccg agccgacgtg ctgattgaaa acggcaaagt cgccgctgtc    120
ggcatgctgg acgccgcgac gccggacaca gttgagcggg ttgactgcga cggcaaatac    180
gtcatgcccg gcgtatcga cgttcacacc cacatcgact ccccctcat ggggaccacc      240 accgccgatg attttgtcag cggaacgatt gcagccgcta ccggcggaac aacgaccatc    300
gtcgatttcg gacagcagct cgccggcaag aacctgctgg aatccgcaga gcgcaccac     360 aaaaaggcgc aggggaaatc cgtcattgat tacggcttcc atatgtgcgt gacgaacctc    420
tatgacaatt tcgattccca tatggcagaa ctgacacagg acggaatctc cagtttcaag    480
gtcttcatgg cctaccgcgg aagcctgatg atcaacgacg gcgaactgtt cgacatcctc    540
aagggagtcg gctccagcgg tgccaaacta tgcgtccacg cagagaacgg cgacgtcatc    600
gacaggatcc ccgccgacct ctacgcccaa ggaaaaaccg gcccgggac ccacgagatc     660 gcacgcccgc cggaatcgga agtcgaagca gtcagccggg ccatcaagat ctcccggatg    720
gccgaggtgc cgctgtattt cgtgcatctt tccacccagg gggccgtcga ggaagtagct    780
gccgcgcaga tgacaggatg gccaatcagc gccgaaacgt gcacccacta cctgtcgctg    840
agccgggaca tctacgacca gccgggattc gagccggcca aagctgtcct cacaccaccg    900
ctgcgcacac aggaacacca ggacgcgttg tggagaggca ttaacaccgg tgcgctcagc    960
gtcgtcagtt ccgaccactg ccccttctgc tttgaggaaa agcagcggat ggggggcagat   1020 gacttccggc agatccccaa cggcgggccc ggcgtggagc accgaatgct cgtgatgtat    1080
gagaccggtg tcgcggaagg aaaaatgacg atcgagaaat cgtcgaggt gactgccgag    1140 aacccggcca agcaattcga tatgtacccg aaaaagggaa caattgcacc gggctccgat    1200
gcagacatca tcgtggtcga ccccaacgga acaaccctca tcagtgccga cacccaaaaa    1260
caaaacatgg actacacgct gttcgaaggc ttcaaaatcc gttgctccat cgaccaggtg    1320
ttctcgcgtg gcgacctgat cagcgtcaaa ggcaatatg tcggcacccg cggccgcggc     1380
gaattcatca gcggagcgc ttggagccac ccgcagttcg aaaaataaaa gcttggctgt     1440
tttggcggat gagagaagat tttcagcctg atacagatta atcgaacg cagaagcggt      1500 ctgataaaac agaatttgcc tggcggcagt agcgcggtgg tcccacctga ccccatgccg    1560
aactcagaag tgaaacgccg tagcgccgat ggtagtgtgg ggtctcccca tgcgagagta    1620
gggaactgcc aggcatcaaa taaaacgaaa ggctcagtcg aaagactggg cctttcgttt    1680
tatctgttgt ttgtcggtga acgctctcct gagtaggaca atccgccgg gagcggattt     1740 gaacgttgcg aagcaacggc ccgagggtg gcgggcagga cgcccgccat aaactgccag    1800
gcatcaaatt aagcagaagg ccatcctgac ggatggcctt tttgcgtttc tacaaactct    1860
tttgtttatt tttctaaata cattcaaata tgtatccgct catgagacaa taaccctgat    1920
```

-continued

```
aaatgcttca ataatattga aaaaggaaga gtatgagtat tcaacatttc cgtgtcgccc   1980
ttattcccctt ttttgcggca ttttgccttc ctgttttgc tcacccagaa acgctggtga    2040
aagtaaaaga tgctgaagat cagttgggtg cacgagtggg ttacatcgaa ctggatctca   2100
acagcggtaa gatccttgag agttttcgcc ccgaagaacg ttttccaatg atgagcactt   2160
ttaaagttct gctatgtggc gcggtattat cccgtgttga cgccgggcaa gagcaactcg   2220
gtcgccgcat acactattct cagaatgact tggttgagta ctcaccagtc acagaaaagc   2280
atcttacgga tggcatgaca gtaagagaat tatgcagtgc tgccataacc atgagtgata   2340
acactgcggc caacttactt ctgacaacga tcggaggacc gaaggagcta accgcttttt   2400
tgcacaacat gggggatcat gtaactcgcc ttgatcgttg ggaaccggag ctgaatgaag   2460
ccataccaaa cgacgagcgt gacaccacga tgcctgtagc aatggcaaca acgttgcgca   2520
aactattaac tggcgaacta cttactctag cttcccggca acaattaata gactggatgg   2580
aggcggataa agttgcagga ccacttctgc gctcggccct tccggctggc tggtttattg   2640
ctgataaatc tggagccggt gagcgtgggt ctcgcggtat cattgcagca ctggggccag   2700
atggtaagcc ctcccgtatc gtagttatct acacgacggg gagtcaggca actatggatg   2760
aacgaaatag acagatcgct gagataggtg cctcactgat taagcattgg taactgtcag   2820
accaagttta ctcatatata ctttagattg atttaaaact tcattttaa tttaaaagga   2880
tctaggtgaa gatcctttt gataatctca tgaccaaaat cccttaacgt gagttttcgt   2940
tccactgagc gtcagacccc gtagaaaaga tcaaaggatc ttcttgagat cctttttttc   3000
tgcgcgtaat ctgctgcttg caaacaaaaa aaccaccgct accagcggtg gtttgtttgc   3060
cggatcaaga gctaccaact cttttttccga aggtaactgg cttcagcaga gcgcagatac   3120
caaatactgt ccttctagtg tagccgtagt taggccacca cttcaagaac tctgtagcac   3180
cgcctacata cctcgctctg ctaatcctgt taccagtggc tgctgccagt ggcgataagt   3240
cgtgtcttac cgggttggac tcaagacgat agttaccgga taaggcgcag cggtcgggct   3300
gaacggggg ttcgtgcaca cagcccagct tggagcgaac gacctacacc gaactgagat   3360
acctacagcg tgagctatga gaaagcgcca cgcttcccga agggagaaag gcggacaggt   3420
atccggtaag cggcagggtc ggaacaggag agcgcacgag ggagcttcca gggggaaacg   3480
cctggtatct ttatagtcct gtcgggtttc gccacctctg acttgagcgt cgatttttgt   3540
gatgctcgtc agggggcgg agcctatgga aaaacgccag caacgcggcc ttttacggt    3600
tcctggcctt ttgctggcct tttgctcaca tgttctttcc tgcgttatcc cctgattctg   3660
tggataaccg tattaccgcc tttgagtgag ctgataccgc tcgccgcagc cgaacgaccg   3720
agcgcagcga gtcagtgagc gaggaagcgg aagagcgcct gatgcggtat tttctcctta   3780
cgcatctgtg cggtatttca caccgcatat atggtgcact ctcagtacaa tctgctctga   3840
tgccgcatag ttaagccagt atacactccg ctatcgctac gtgactgggt catggctgcg   3900
ccccgacacc cgccaacacc cgctgacgcg ccctgacggg cttgtctgct cccggcatcc   3960
gcttacagac aagctgtgac cgtctccggg agctgcatgt gtcagaggtt ttcaccgtca   4020
tcaccgaaac gcgcgaggca gctgcggtaa agctcatcag cgtggtcgtg aagcgattca   4080
cagatgtctg cctgttcatc cgcgtccagc tcgttgagtt tctccagaag cgttaatgtc   4140
tggcttctga taaagcgggc catgttaagg gcggtttttt cctgtttggt cacttgatgc   4200
ctccgtgtaa gggggaattt ctgttcatgg ggtaatgat accgatgaaa cgagagagga   4260
tgctcacgat acgggttact gatgatgaac atgcccggtt actggaacgt tgtgagggta   4320
```

-continued

```
aacaactggc ggtatggatg cggcgggacc agagaaaaat cactcaggt caatgccagc    4380 gcttcgttaa tacagatgta ggtgttccac agggtagcca gcagcatcct gcgatgcaga    4440
tccggaacat aatggtgcag ggcgctgact tccgcgtttc cagactttac gaaacacgga    4500
aaccgaagac cattcatgtt gttgctcagg tcgcagacgt tttgcagcag cagtcgcttc    4560
acgttcgctc gcgtatcggt gattcattct gctaaccagt aaggcaaccc cgccagccta    4620
gccgggtcct caacgacagg agcacgatca tgcgcacccg tggccaggac ccaacgctgc    4680
ccgagatgcg ccgcgtgcgg ctgctggaga tggcggacgc gatggatatg ttctgccaag    4740
ggttggtttg cgcattcaca gttctccgca agaattgatt ggctccaatt cttggagtgg    4800
tgaatccgtt agcgaggtgc cgccggcttc cattcaggtc gaggtggccc ggctccatgc    4860
accgcgacgc aacgcgggga ggcagacaag gtatagggcg gcgcctacaa tccatgccaa    4920
cccgttccat gtgctcgccg aggcggcata atcgccgtg acgatcagcg gtccagtgat    4980
cgaagttagg ctggtaagag ccgcgagcga tccttgaagc tgtccctgat ggtcgtcatc    5040
tacctgcctg acagcatgg cctgcaacgc gggcatcccg atgccgccgg aagcgagaag    5100
aatcataatg gggaaggcca tccagcctcg cgtcgcgaac gccagcaaga cgtagcccag    5160
cgcgtcggcc gccatgccgg cgataatggc ctgcttctcg ccgaaacgtt tggtggcggg    5220
accagtgacg aaggcttgag cgagggcgtg caagattccg aataccgcaa gcgacaggcc    5280
gatcatcgtc gcgctccagc gaaagcggtc ctcgccgaaa atgacccaga gcgctgccgg    5340
cacctgtcct acgagttgca tgataaagaa gacagtcata agtgcggcga cgatagtcat    5400
gccccgcgcc caccggaagg agctgactgg gttgaaggct ctcaagggca tcggtcgacg    5460
ctctccctta tgcgactcct gcattaggaa gcagcccagt agtaggttga ggccgttgag    5520
caccgccgcc gcaaggaatg gtgcatgctc gatggctacg agggcagaca gtaagtggat    5580
ttaccataat cccttaattg tacgcaccgc taaaacgcgt tcagcgcgat cacggcagca    5640
gacaggtaaa aatggcaaca aaccacccta aaaactgcgc gatcgcgcct gataaatttt    5700
aaccgtatga ataccatgc aaccagaggg tacaggccac attacccca cttaatccac    5760 tgaagctgcc atttttcatg gtttcaccat cccagcgaag ggccatgcat gcatcgaaat    5820
taatacgacg aaattaatac gactcactat agggcaattg cgatcaccac aattcagcaa    5880
attgtgaaca tcatcacgtt catctttccc tggttgccaa tggcccattt tcctgtcagt    5940
aacgagaagg tcgcgaattc aggcgctttt tagactggtc gtaatgaac    5989
```

<210> SEQ ID NO 16
<211> LENGTH: 6958
<212> TYPE: DNA
<213> ORGANISM: Artificial sequence
<220> FEATURE:
<223> OTHER INFORMATION: plasmid containing sequence encoding hydantoin racemase of Arthrobacter crystallopoietes

<400> SEQUENCE: 16

```
aattcttaag aaggagatat acatatggcg aaaaacttga tgctcgcggt cgctcaagtc      60
ggcggtatcg atagttcgga atcaagaccc gaagtcgtcg cccgcttgat tgccctgctg     120
gaagaagcag cttcccaggg cgcggaactg gtggtctttc ccgaactcac gctgaccacg     180
ttcttcccgc gtacctggtt cgaagaaggc gacttcgagg aatacttcga taaatccatg     240
cccaatgacg acgtcgcgcc cctttttcgaa cgcgccaaag accttggcgt gggcttctac     300
ctcggatacg cggaactgac cagtgatgag aagcggtaca acacatcaat tctggtgaac     360
```

-continued

| | |
|---|---|
| aagcacggcg acatcgtcgg caagtaccgc aagatgcatc tgccgggcca cgccgataac | 420 |
| cgggaaggac tacccaacca gcaccttgaa aagaaatact ccgcgaagg agatctcgga | 480 |
| ttcggtgtct tcgacttcca cggcgtgcag gtcggaatgt gtctctgcaa cgaccggcga | 540 |
| tggccggagg tctaccgctc tttggccctg cagggagcag agctcgtcgt cctgggctac | 600 |
| aacaccccg atttcgttcc cggctggcag gaagagcctc acgcgaagat gttcacgcac | 660 |
| cttctttcac ttcaggcagg ggcataccag aactcggtat tgtggcggc tgccggcaag | 720 |
| tcgggcttcg aagacgggca ccacatgatc ggcggatcag cggtcgccgc gcccagcggc | 780 |
| gaaatcctgg caaaagcagc cggcgagggc gatgaagtcg tcgttgtgaa agcagacatc | 840 |
| gacatgggca agcccctataa ggaaagcgtc ttcgacttcg ccgcccatcg gcgccccgac | 900 |
| gcatacggca tcatcgccga aggaaaggg cggggcgccc cactgcccgt cccgttcaac | 960 |
| gtgaatgact aaggatccga aggagatata catatggatg caaagctact ggttggcggc | 1020 |
| actattgttt cctcgaccgg caaaatccga gccgacgtgc tgattgaaaa cggcaaagtc | 1080 |
| gccgctgtcg gcatgctgga cgccgcgacg ccggacacag ttgagcgggt tgactgcgac | 1140 |
| ggcaaatacg tcatgcccgg cggtatcgac gttcacaccc acatcgactc cccctcatg | 1200 |
| gggaccacca ccgccgatga ttttgtcagc ggaacgattg cagccgctac cggcggaaca | 1260 |
| acgaccatcg tcgatttcgg acagcagctc gccggcaaga acctgctgga atccgcagac | 1320 |
| gcgcaccaca aaaaggcgca ggggaaatcc gtcattgatt acggcttcca tatgtgcgtg | 1380 |
| acgaacctct atgacaattt cgattcccat atggcagaac tgacacagga cggaatctcc | 1440 |
| agtttcaagg tcttcatggc ctaccgcgga agcctgatga tcaacgacgg cgaactgttc | 1500 |
| gacatcctca agggagtcgg ctccagcggt gccaaactat gctccacgc agagaacggc | 1560 |
| gacgtcatcg acaggatcgc cgccgacctc tacgcccaag gaaaaaccgg gcccgggacc | 1620 |
| cacgagatcg cacgcccgcc ggaatcggaa gtcgaagcag tcagccgggc catcaagatc | 1680 |
| tcccggatgg ccgaggtgcc gctgtatttc gtgcatcttt ccacccaggg ggccgtcgag | 1740 |
| gaagtagctg ccgcgcagat gacaggatgg ccaatcagcg ccgaaacgtg cacccactac | 1800 |
| ctgtcgctga gccgggacat ctacgaccag ccgggattcg agccggccaa agctgtcctc | 1860 |
| acaccaccgc tgcgcacaca ggaacaccag gacgcgttgt ggagaggcat taacaccggt | 1920 |
| gcgctcagcg tcgtcagttc cgaccactgc cccttctgct ttgaggaaaa gcagcggatg | 1980 |
| ggggcagatg acttccggca gatccccaac ggcgggcccg gcgtggagca ccgaatgctc | 2040 |
| gtgatgtatg agaccggtgt cgcggaagga aaaatgacga tcgagaaatt cgtcgaggtg | 2100 |
| actgccgaga acccggccaa gcaattcgat atgtacccga aaaagggaac aattgcaccg | 2160 |
| ggctccgatg cagacatcat cgtggtcgac cccaacggaa caaccctcat cagtgccgac | 2220 |
| acccaaaaac aaaacatgga ctacacgctg ttcgaaggct tcaaaatccg ttgctccatc | 2280 |
| gaccaggtgt tctcgcgtgg cgacctgatc agcgtcaaag gcgaatatgt cggcacccgc | 2340 |
| ggccgcggcg aattcatcaa gcggagcgct tggagccacc gcagttcga aaataaaag | 2400 |
| cttggctgtt ttggcggatg agagaagatt ttcagcctga tacagattaa atcagaacgc | 2460 |
| agaagcggtc tgataaaaca gaatttgcct ggcggcagta gcgcggtggt cccacctgac | 2520 |
| cccatgccga actcagaagt gaaacgccgt agcgccgatg gtagtgtggg gtctccccat | 2580 |
| gcgagagtag ggaactgcca ggcatcaaat aaaacgaaag gctcagtcga aagactgggc | 2640 |
| cttcgttt atctgttgtt tgtcggtgaa cgctctcctg agtaggacaa atccgccggg | 2700 |

-continued

```
agcggatttg aacgttgcga agcaacggcc cggagggtgg cgggcaggac gcccgccata    2760
aactgccagg catcaaatta agcagaaggc catcctgacg gatggccttt ttgcgtttct    2820
acaaactctt ttgtttattt ttctaaatac attcaaatat gtatccgctc atgagacaat    2880
aaccctgata aatgcttcaa taatattgaa aaggaagag tatgagtatt caacatttcc     2940
gtgtcgccct tattcccttt tttgcggcat tttgccttcc tgttttgct cacccagaaa    3000
cgctggtgaa agtaaaagat gctgaagatc agttgggtgc acgagtgggt tacatcgaac    3060
tggatctcaa cagcggtaag atccttgaga gttttcgccc cgaagaacgt tttccaatga    3120
tgagcacttt taaagttctg ctatgtggcg cggtattatc ccgtgttgac gccgggcaag    3180
agcaactcgg tcgccgcata cactattctc agaatgactt ggttgagtac tcaccagtca    3240
cagaaaagca tcttacggat ggcatgacag taagagaatt atgcagtgct gccataacca    3300
tgagtgataa cactgcggcc aacttacttc tgacaacgat cggaggaccg aaggagctaa    3360
ccgctttttt gcacaacatg ggggatcatg taactcgcct tgatcgttgg gaaccggagc    3420
tgaatgaagc cataccaaac gacgagcgtg acaccacgat gcctgtagca atggcaacaa    3480
cgttgcgcaa actattaact ggcgaactac ttactctagc ttcccggcaa caattaatag    3540
actggatgga ggcggataaa gttgcaggac cacttctgcg ctcggccctt ccggctggct    3600
ggtttattgc tgataaatct ggagccggtg agcgtgggtc tcgcggtatc attgcagcac    3660
tggggccaga tggtaagccc tcccgtatcg tagttatcta cacgacgggg agtcaggcaa    3720
ctatggatga acgaaataga cagatcgctg agataggtgc ctcactgatt aagcattggt    3780
aactgtcaga ccaagtttac tcatatatac tttagattga tttaaaactt catttttaat    3840
ttaaaaggat ctaggtgaag atcctttttg ataatctcat gaccaaaatc ccttaacgtg    3900
agttttcgtt ccactgagcg tcagacccg tagaaaagat caaaggatct cttgagatc     3960
ctttttttct gcgcgtaatc tgctgcttgc aaacaaaaaa accaccgcta ccagcggtgg    4020
tttgtttgcc ggatcaagag ctaccaactc tttttccgaa ggtaactggc ttcagcagag    4080
cgcagatacc aaatactgtc cttctagtgt agccgtagtt aggccaccac ttcaagaact    4140
ctgtagcacc gcctacatac ctcgctctgc taatcctgtt accagtggct gctgccagtg    4200
gcgataagtc gtgtcttacc gggttggact caagacgata gttaccggat aaggcgcagc    4260
ggtcgggctg aacggggggt tcgtgcacac agcccagctt ggagcgaacg acctacaccg    4320
aactgagata cctacagcgt gagctatgag aaagcgccac gcttcccgaa gggagaaagg    4380
cggacaggta tccggtaagc ggcagggtcg gaacaggaga gcgcacgagg gagcttccag    4440
ggggaaacgc ctggtatctt tatagtcctg tcgggtttcg ccacctctga cttgagcgtc    4500
gatttttgtg atgctcgtca ggggggcgga gcctatggaa aaacgccagc aacgcggcct    4560
ttttacggtt cctggccttt tgctggcctt ttgctcacat gttctttcct gcgttatccc    4620
ctgattctgt ggataaccgt attaccgcct ttgagtgagc tgataccgct cgccgcagcc    4680
gaacgaccga gcgcagcgag tcagtgagcg aggaagcgga agagcgcctg atgcggtatt    4740
ttctccttac gcatctgtgc ggtatttcac accgcatata tggtgcactc tcagtacaat    4800
ctgctctgat gccgcatagt taagccagta tacactccgc tatcgctacg tgactgggtc    4860
atggctgcgc cccgacaccc gccaacaccc gctgacgcgc cctgacgggc ttgtctgctc    4920
ccggcatccg cttacagaca agctgtgacc gtctccggga gctgcatgtg tcagaggttt    4980
tcaccgtcat caccgaaacg cgcgaggcag ctgcggtaaa gctcatcagc gtggtcgtga    5040
agcgattcac agatgtctgc ctgttcatcc gcgtccagct cgttgagttt ctccagaagc    5100
```

```
gttaatgtct ggcttctgat aaagcgggcc atgttaaggg cggttttttc ctgtttggtc    5160
acttgatgcc tccgtgtaag ggggaatttc tgttcatggg ggtaatgata ccgatgaaac    5220
gagagaggat gctcacgata cgggttactg atgatgaaca tgcccggtta ctggaacgtt    5280
gtgagggtaa acaactggcg gtatggatgc ggcgggacca gagaaaaatc actcagggtc    5340
aatgccagcg cttcgttaat acagatgtag gtgttccaca gggtagccag cagcatcctg    5400
cgatgcagat ccggaacata atggtgcagg gcgctgactt ccgcgtttcc agactttacg    5460
aaacacggaa accgaagacc attcatgttg ttgctcaggt cgcagacgtt ttgcagcagc    5520
agtcgcttca cgttcgctcg cgtatcggtg attcattctg ctaaccagta aggcaacccc    5580
gccagcctag ccgggtcctc aacgacagga gcacgatcat gcgcacccgt ggccaggacc    5640
caacgctgcc cgagatgcgc cgcgtgcggc tgctggagat ggcggacgcg atggatatgt    5700
tctgccaagg gttggtttgc gcattcacag ttctccgcaa gaattgattg gctccaattc    5760
ttggagtggt gaatccgtta gcgaggtgcc gccggcttcc attcaggtcg aggtggcccg    5820
gctccatgca ccgcgacgca acgcggggag gcagacaagg tatagggcgg cgcctacaat    5880
ccatgccaac ccgttccatg tgctcgccga ggcggcataa atcgccgtga cgatcagcgg    5940
tccagtgatc gaagttaggc tggtaagagc cgcgagcgat ccttgaagct gtccctgatg    6000
gtcgtcatct acctgcctgg acagcatggc ctgcaacgcg ggcatcccga tgccgccgga    6060
agcgagaaga atcataatgg ggaaggccat ccagcctcgc gtcgcgaacg ccagcaagac    6120
gtagcccagc gcgtcggccg ccatgccggc gataatggcc tgcttctcgc cgaaacgttt    6180
ggtggcggga ccagtgacga aggcttgagc gagggcgtgc aagattccga ataccgcaag    6240
cgacaggccg atcatcgtcg cgctccagcg aaagcggtcc tcgccgaaaa tgacccagag    6300
cgctgccggc acctgtccta cgagttgcat gataaagaag acagtcataa gtgcggcgac    6360
gatagtcatg ccccgcgccc accggaagga gctgactggg ttgaaggctc tcaagggcat    6420
cggtcgacgc tctcccttat gcgactcctg cattaggaag cagcccagta gtaggttgag    6480
gccgttgagc accgccgccg caaggaatgg tgcatgctcg atggctacga gggcagacag    6540
taagtggatt taccataatc ccttaattgt acgcaccgct aaaacgcgtt cagcgcgatc    6600
acggcagcag acaggtaaaa atggcaacaa accaccctaa aaactgcgcg atcgcgcctg    6660
ataaatttta accgtatgaa tacctatgca accagagggt acaggccaca ttaccccac     6720 ttaatccact gaagctgcca tttttcatgg tttcaccatc ccagcgaagg gccatgcatg    6780
catcgaaatt aatacgacga aattaatacg actcactata gggcaattgc gatcaccaca    6840
attcagcaaa ttgtgaacat catcacgttc atctttccct ggttgccaat ggcccatttt    6900
cctgtcagta acgagaaggt cgcgaattca ggcgcttttt agactggtcg taatgaac      6958
```

SCREENING PROCESS FOR HYDANTOIN RACEMASES

CROSS REFERENCE TO RELATED APPLICATIONS

The present application represents U.S. national stage of international application PCT/EP2004/005239, which had an international filing date of May 15, 2004, and which was published in English under PCT Article 21(2) on Dec. 23, 2004. The international application claims priority to German applications 103 26 109.5, filed on Jun. 6, 2003 and 10 2004 022 065.4, filed on May 5, 2004. The priority applications are hereby incorporated by reference in their entirety.

THE FIELD OF THE INVENTION

The present invention relates to a screening process for the detection of improved hydantoin racemases, to novel hydantoin racemases themselves and to their use in the preparation of N-carbamoyl-amino acids.

These optically active compounds are compounds that are frequently used in organic synthesis for the preparation of, for example, active ingredients having biological activity. They are also present in chiral auxiliaries, for example in the form of the amino alcohols (Evans reagents).

BACKGROUND OF THE INVENTION

The enzymatic hydrolysis of 5-substituted hydantoins to N-carbamoyl-amino acids and the further reaction thereof to the corresponding enantiomerically-enriched amino acids is a standard method in organic chemistry ("Enzyme Catalysis in Organic Synthesis", Eds.: Drauz, Waldmann, VCH, 1$^{st}$ and 2$^{nd}$ Ed.). The enantiodifferentiation can be carried out either at the stage of the hydantoin hydrolysis by means of hydantoinases or alternatively during the cleavage of the N-carbamoyl-amino acids by means of enantioselective carbamoylases. Because the enzymes each convert only one optical antipode of the corresponding compound, it is attempted to racemise the other in the mixture (in situ) in order to ensure the complete conversion of the hydantoin, which can readily be prepared racemically, into the corresponding enantiomerically enriched amino acid. The racemisation can proceed either at the stage of the hydantoins by means of chemical (base, acid, elevated temperature) or enzymatic processes or alternatively at the stage of the N-carbamoyl-amino acids by means of, for example, acetylamino acid racemases (DE10050124). By its nature, the latter variant is only successful if enantioselective carbamoylases are used. The following scheme illustrates this fact.

Scheme 1:

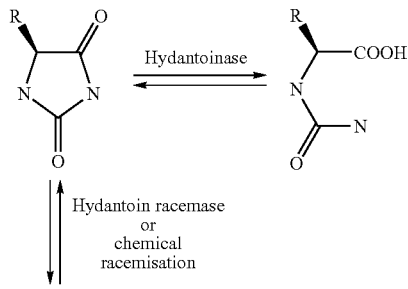

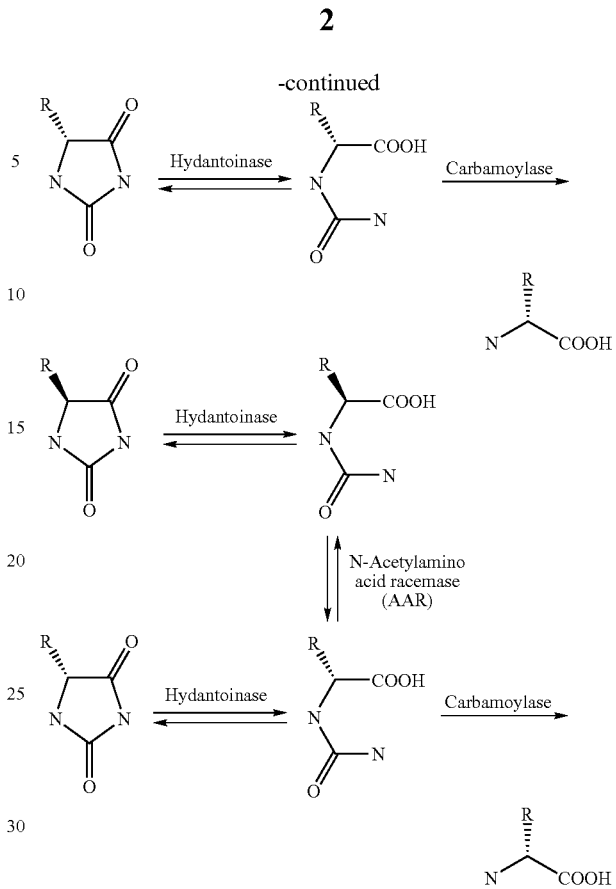

For aromatic substrates, the rate of the chemical racemisation of the hydantoins, as shown in Table 1, is sufficiently high to ensure high space-time yields for the preparation of amino acids by the hydantoinase process. For aliphatic hydantoins, such as isobutyl-, methyl- and isopropyl-hydantoin, however, the racemisation represents a considerable bottleneck in the synthesis of aliphatic amino acids.

TABLE 1

Racemisation constants of hydantoins at 40° C., pH 8.5 determined by initial rates according to a first-order reaction ($-k_{rac} = \ln([a]/[a_0])$) from: Hydrolysis and Formation of Hydantoins (Chpt. B 2.4). Syldatk, C. and Pietzsch, M. In: Enzyme catalysis in organic synthesis (Eds.: K. Drauz & H. Waldmann), VCH, 1$^{st}$ and 2$^{nd}$ Ed.).

| 5'-substituent | $k_{rac}$ (h$^{-1}$) | $t_{1/2}$ (h) |
| --- | --- | --- |
| Phenyl | 2.59 | 0.27 |
| Methylthioethyl | 0.12 | 5.82 |
| Isobutyl | 0.032 | 21.42 |
| Methyl | 0.02 | 33.98 |
| Isopropyl | 0.012 | 55.90 |

This problem manifests itself, for example, in the preparation, described in EP759475, of enantiomerically enriched tert.-butylhydantoin by means of the hydantoinase process. In this case, the complete conversion of 32 mM tert.-butylhydantoin with 1.5 kU R-hydantoinase required 8 days at pH 8.5 and 4 days at pH 9.5. The low space-time yield is in fact caused by the only slow chemical racemisation of tert.-butylhydantoin ($k_{rac}$=0.009 h$^{-1}$ at 50° C. and pH 8.5).

There are known from the prior art hydantoin racemases from microorganisms of the genus Pseudomonas, Microbacterium, Agrobacterium and Arthrobacter (lit.:

JP04271784; EP1188826; Cloning and characterization of genes from *Agrobacterium* sp. IP I-671 involved in hydantoin degradation. Hils, M.; Muench, P.; Altenbuchner, J.; Syldatk, C.; Mattes, R. Applied Microbiology and Biotechnology (2001), 57(5-6), 680-688; A new razemase for 5-monosubstituted hydantoins. Pietzsch, Markus; Syldatk, Christoph; Wagner, Fritz. Ann. N. Y. Acad. Sci. (1992), 672 (*Enzyme Engineering XI*), 478-83. Lickefett, Holger; Krohn, Karsten; Koenig, Wilfried A.; Gehrcke, Barbel; Syldatk, Christoph. Tetrahedron: Asymmetry (1993), 4(6), 1129-35; Purification and characterization of the hydantoin razemase of *Pseudomonas* sp. strain NS671 expressed in *Escherichia coli*. Watabe, Ken; Ishikawa, Takahiro; Mukohara, Yukuo; Nakamura, Hiroaki. J. Bacteriol. (1992), 174(24), 7989-95).

Of the hydantoin racemases from *Arthrobacter aurescens* DSM 3745, *Pseudomonas* sp. NS671 and *Microbacterium liquefaciens*, it is known that these enzymes racemise aliphatic hydantoins, such as, for example, isopropylhydantoin or isobutylhydantoin, only weakly. It is also known that the hydantoin racemases from *Arthrobacter aurescens* DSM 3747 preferentially convert aromatic hydantoins, such as indolylmethylhydantoin or benzylhydantoin, whereas aliphatic hydantoins, such as methylthioethylhydantoin, are converted comparatively weakly or, in the case of isopropylhydantoin, are not converted at all (A new razemase for 5-monosubstituted hydantoins. Pietzsch, Markus; Syldatk, Christoph; Wagner, Fritz. Ann. N. Y. Acad. Sci. (1992), 672 (Enzyme Engineering XI), 478-83.).

The low activity of hydantoin racemases therefore frequently limits the economic potential of this route.

DESCRIPTION OF THE INVENTION

In order to enable as many hydantoin racemases as possible to be checked in a suitable time for their potential to racemise aliphatic hydantoins, the object of the present invention was inter alia to provide a suitable screening process for hydantoin racemases. Moreover, the screening process according to the invention should be usable as a component of a mutagenesis process for obtaining new and improved hydantoin racemases. It was also an object of the present invention to provide novel hydantoin racemases which are superior to the hydantoin racemases of the prior art at least in terms of selectivity and/or activity and/or stability.

This object is achieved according to the claims. Claim 1 relates to a screening process for hydantoin racemases. Dependent claims 2 to 4 indicate advantageous embodiments of the screening process. Claim 5 is concerned with a mutagenesis process for the preparation of novel hydantoin racemases using the screening process according to the invention. Claims 6 to 11 relate to novel hydantoin racemases and to the nucleic acid sequences coding therefor and their use. Claims 12 to 14 are directed towards vehicles containing the hydantoin racemases according to the invention, or particular primers for their preparation.

By the provision of a screening process for hydantoin racemases, in which a) an enantioselective hydantoinase and b) the hydantoin racemase to be tested, which has a slower conversion rate compared with the hydantoinase under a), are allowed to act on c) a chiral hydantoin, which is used in the opposite enantiomerically enriched form to the selectivity of the hydantoinase, and d) the resulting N-carbamoyl-amino acid or the freed protons are detected in a time-dependent manner, it becomes possible in a surprisingly simple and yet advantageous manner to check a large number of hydantoin racemases in a short time for their ability to racemise hydantoins in an improved manner.

By the use of an L-enantiomer of a 5'-monosubstituted hydantoin and the use of a D-selective hydantoinase which, on the basis of its enantioselectivity, preferably rapidly hydrolyses the resulting D-enantiomer of the hydantoin, the racemisation rate and hence the activity of the hydantoin racemase can be measured in a simple manner by the formation of the N-carbamoyl-D-amino acid or by freed protons. The N-carbamoyl-amino acid can be quantified by methods known to the person skilled in the art, such as, for example, HPLC or colorimetric methods. Quantification via protons can be carried out in a simple manner via pH indicators, preferably cresol red. It should be noted that both D- and L-enantiomers of hydantoins having different optionally aliphatic 5'-substituents can be used in the process. When D-hydantoins are used, corresponding L-selective hydantoinases are to be used in the screening process.

In the process according to the invention there are advantageously used aliphatic hydantoins substituted in the 5'-position. In this context, aliphatically substituted hydantoins are understood to mean a system which has in the 5'-position on the hydantoin heterocycle a radical which is bonded to the heterocycle via a carbon atom having sp$^3$-hybridisation. Preferred 5'-substituents are methyl, ethyl, butyl, propyl, tertiary butyl, isopropyl and isobutyl. Ethylhydantoin is very particularly preferred.

There may be used as hydantoinases any hydantoinases known in the literature which enantioselectively hydrolyse the hydantoin enantiomer formed via the hydantoin racemase, it being necessary for this hydrolysis to be more rapid than the racemisation rate. Preferred hydantoinases are the commercial hydantoinases 1 & 2 from Roche, the hydantoinases of the genera *Agrobacterium, Arthrobacter, Bacillus, Pseudomonas, Flavobacterium, Pasteurella, Microbacterium, Vigna, Ochrobactrum, Methanococcus, Burkholderia* and *Streptomyces*. (Hils, M.; Muench, P.; Altenbuchner, J.; Syldatk, C.; Mattes, R. Cloning and characterization of genes from *Agrobacterium* sp. IP I-671 involved in hydantoin degradation. Applied Microbiology and Biotechnology (2001), 57(5-6), 680-688. Soong, C.-L.; Ogawa, J.; Shimizu, S. Cyclic ureide and imide metabolism in microorganisms producing a D-hydantoinase useful for D-amino acid production. Journal of Molecular Catalysis B: Enzymatic (2001), 12(1-6), 61-70. Wiese, Anja; Wilms, Burkhard; Syldatk, Christoph; Mattes, Ralf; Altenbuchner, Josef. Cloning, nucleotide sequence and expression of a hydantoinase and carbamoylase gene from *Arthrobacter aurescens* DSM 3745 in *Escherichia coli* and comparison with the corresponding genes from *Arthrobacter aurescens* DSM 3747. Applied Microbiology and Biotechnology (2001), 55(6), 750-757. Yin, Bang-Ding; Chen, Yi-Chuan; Lin, Sung-Chyr; Hsu, Wen-Hwei. Production of D-amino acid precursors with permeabilized recombinant *Escherichia coli* with D-hydantoinase activity. Process Biochemistry (Oxford) (2000), 35(9), 915-921. Park, Joo-Ho; Kim, Geun-Joong; Lee, Seung-Goo; Lee, Dong-Cheol; Kim, Hak-Sung. Purification and characterization of thermostable D-hydantoinase from *Bacillus thermocatenulatus* GH-2. Applied Biochemistry and Biotechnology (1999), 81(1), 53-65; Pozo, C.; Rodelas, B.; de la Escalera, S.; Gonzalez-Lopez, J. D,L-Hydantoinase activity of an Ochrobactrum anthropi strain. Journal of Applied Microbiology (2002), 92(6), 1028-1034; Chung, Ji Hyung; Back, Jung Ho; Lim, Jae-Hwan; Park, Young-In; Han, Ye Sun. Thermostable hydantoinase from a hyperthermophilic archaeon, *Methanococcus jannaschii*. Enzyme and Microbial Technology (2002), 30(7), 867-874; Xu, Zhen; Jiang, Weihong; Jiao, Ruishen; Yang, Yunliu. Cloning, sequencing and high expression in *Escherichia coli* of D-hydantoinase gene from *Burkholderia pickettii*. Shengwu Gongcheng Xuebao (2002), 18(2), 149-154; Las Heras-Vazquez, Francisco Javier; Martinez-Rodriguez, Sergio; Mingorance-Cazorla, Lydia; Clemente-Jimenez, Josefa Maria; Rodriguez-Vico, Felipe. Overexpression and characterization of hydantoin racemase from *Agrobacterium tumefaciens* C58. Biochemical and Biophysical Research Communications (2003), 303 (2), 541-547; DE 3535987; EP 1275723; US 6087136; WO 0281626; US 2002045238; DE 4328829; WO 9400577; WO 9321336; JP 04325093; NL 9001680; JP 2003024074; Wb 0272841; WO 0119982; WO 9620275).

The use of the hydantoinase from *Arthrobacter crystallopoietes*, especially from DSM 20117, is very particularly preferred.

As already indicated, the conversion rate of the hydantoinase should be superior to that of the racemase. The ratio of the rate constants of the hydantoinase to the hydantoin racemase ($k_{hyd}/k_{rac}$) is preferably >2, particularly preferably >10 and very particularly preferably >50.

The invention also provides a process for the preparation of improved hydantoin racemases, which is distinguished by the fact that
a) the nucleic acid sequence coding for the hydantoin racemase is subjected to a mutagenesis,
b) the nucleic acid sequences obtainable from a) are cloned into a suitable vector and the vector is transferred into a suitable expression system, and
c) the resulting hydantoin racemases having improved activity and/or selectivity and/or stability are detected by means of a screening process according to the invention and isolated.

There may be used as starting genes for the mutagenesis of the hydantoin racemases any known hydantoin racemase genes mentioned in the listed literature. Preference is given to the hydantoin racemase genes of *Arthobacter*, *Pseudomonas*, *Agrobacterium* and *Micrococcus* (Wiese A; Pietzsch M; Syldatk C; Mattes R; Altenbuchner J Hydantoin racemase from *Arthrobacter aurescens* DSM 3747: heterologous expression, purification and characterization. JOURNAL OF BIOTECHNOLOGY (Jul. 14, 2000), 80(3), 217-30; Watabe K; Ishikawa T; Mukohara Y; Nakamura H Purification and characterization of the hydantoin racemase of *Pseudomonas* sp. strain NS671 expressed in *Escherichia coli*. JOURNAL OF BACTERIOLOGY (December 1992), 174(24), 7989-95; Las Heras-Vazquez, Francisco Javier; Martinez-Rodriguez, Sergio; Mingorance-Cazorla, Lydia; Clemente-Jimenez, Josefa Maria; Rodriguez-Vico, Felipe. Overexpression and characterization of hydantoin racemase from Agrobacterium tumefaciens C58. Biochemical and Biophysical Research Communications (2003), 303(2), 541-547; EP 1188826). Very particular preference is given to the hydantoin racemase gene from *Arthrobacter aurescens*, which codes for the protein sequence in Seq.ID.No. 2.

For the mutagenesis of the hydantoin racemase there may be used any methods known in the literature, such as, for example, random mutagenesis, saturation mutagenesis, cassette mutagenesis or recombination methods (May, Oliver; Voigt, Christopher A.; Arnold, Frances H. Enzyme engineering by directed evolution. Enzyme Catalysis in Organic Synthesis (2nd Edition) (2002), 1 95-138; Bio/Technology 1991, 9, 1073-1077; Horwitz, M. and Loeb, L., Promoters Selected From Random DNA-Sequences, Proc Natl Acad Sci USA 83, 1986, 7405-7409; Dube, D. and L. Loeb, Mutants Generated By The Insertion Of Random Oligonucleotides Into The Active-Site Of The Beta-Lactamase Gene, Biochemistry 1989, 28, 5703-5707; Stemmer, P. C., Rapid evolution of a protein in vitro by DNA shuffling, Nature 1994, 370, 389-391 and Stemmer, P. C., DNA shuffling by random fragmentation and reassembly: In vitro recombination for molecular evolution. Proc Natl Acad Sci USA 91, 1994, 10747-10751).

The cloning and expression can be carried out as in the literature mentioned hereinbelow. The process can be carried out several times in succession, optionally with varying mutagenesis strategies.

The invention also provides rec-polypeptides or the nucleic acid sequences coding therefor, which are obtainable by the mutagenesis process mentioned above.

Another aspect of the invention is the use of the polypeptides so prepared in the preparation of chiral enantiomerically enriched N-carbamoyl-amino acids or amino acids. The nucleic acid sequences prepared according to the invention can be used in the preparation of whole cell catalysts.

Hydantoin racemases which have in position 79 an amino acid substitution with an amino acid selected from the group consisting of A, R, N, D, C, Q, E, H, I, L, K, M, F, P, S, T, Y and V also form part of the present invention. It is interesting that the amino acids surrounding this position are retained completely for many hydantoin racemases. The consensus sequence reads: $FX_1DX_2GL$ (Seq.ID.No. 1), wherein $X_2$ represents P or T and $X_1$ represents W or G. Preferred mutants therefore contain the above-mentioned consensus sequence, $X_1$ preferably representing an amino acid selected from the group consisting of A, R, N, D, C, Q, E, H, I, L, K, M, F, P, S, T, Y and V. $X_1$ corresponds to position 79. Preferred mutants are shown in Table 2.

TABLE 2

| Mutant name | Mutation (codon) | Mutation $X_1$ (amino acid) | Activity change | Seq. ID No. |
|---|---|---|---|---|
| 3CH11 | GGG -> GAG | G79E | 2 | 5 |
| 1BG7 | GGG -> AGG | G79R | 2 | 3 |
| BB5 | GGG -> TTG | G79L | 4 | 9 |
| AE3 | GGG -> CAG | G79Q | 4 | 7 |

Further extremely advantageous combinations of $X_1$ and $X_2$ hydantoin racemases are listed in Table 3 below.

TABLE 3

Advantageous combinations of $X_1$ and $X_2$ in the consensus motif $FX_1DX_2GL$

| $X_1$ | L | E | Q | R | L | E | Q | R |
|---|---|---|---|---|---|---|---|---|
| $X_2$ | P | P | P | P | T | T | T | T |

It is particularly advantageous if the hydantoin racemases contain the above-mentioned consensus region and additionally exhibit a homology of >40% with the hydantoin racemase from DSM 20117.

The invention also provides isolated nucleic acid sequences coding for a hydantoin racemase selected from the group:
a) a nucleic acid sequence coding for a hydantoin racemase according to the invention,
b) a nucleic acid sequence which hybridises under stringent conditions with the nucleic acid sequence coding for a hydantoin racemase according to the invention or with the sequence complementary thereto, c) a nucleic acid sequence according to Seq.ID.No. 3, 5, 7 or 9 or a nucleic acid sequence-having a homology of >80% therewith, d) a nucleic acid sequence containing 15 successive nucleotides of sequences Seq.ID.No. 3, 5, 7 or 9.

With regard to point d), it is preferred for the nucleotide sequence according to the invention to contain 20, more preferably 25, yet more preferably 30, 31, 32, 33, 34 and most preferably more than 34 identical consecutive nucleic acids of the sequences Seq.ID.No. 3, 5, 7 or 9.

As mentioned, the invention also includes nucleic acid sequences which hybridise under stringent conditions with the single-strand nucleic acid sequences according to the invention or with their complementary single-strand nucleic acid sequences (b), or nucleic acid sequences which are alike in sequence sections (d). Particular gene probes or the primers necessary for a PCR, for example, are to be regarded as such.

Coupling of hydantoin racemase and hydantoinase and optionally carbamoylase can be carried out by bringing together the free or immobilised enzymes. However, it is preferred for the hydantoinase to be expressed in the same cell together with the hydantoin racemase and/or the carbamoylase (whole cell catalyst).

The nucleic acid sequences according to the invention can therefore be cloned into a whole cell catalyst as a constituent of a gene in a manner analogous to that in DE10234764 and the literature cited therein.

Provided that the latter then also contains genes for a hydantoinase and/or carbamoylase, it is capable of converting racemic hydantoins completely into enantiomerically enriched amino acids. Without a cloned carbamoylase gene, the reaction stops at the stage of the N-carbamoyl-amino acids.

The host organism used is preferably an organism as mentioned in DE10155928. The advantage of such an organism is the simultaneous expression of all the enzymes involved, with which only a rec-organism must be used for the total reaction.

In order to match the expression of the enzymes in respect of their conversion rates, the corresponding coding nucleic acid sequences can be cloned into different plasmids with different copy numbers and/or promoters of different strengths can be used for a different strength of expression of the nucleic acid sequences. In such matched enzyme systems, there is advantageously no accumulation of an intermediate compound which may have an inhibiting action, and the reaction under consideration can proceed at an optimum overall rate. This is sufficiently well known to the person skilled in the art, however (Gellissen, G.; Piontek, M.; Dahlems, U.; Jenzelewski, V.; Gavagan, J. W.; DiCosimo, R.; Anton, D. L.; Janowicz, Z. A. (1996), Recombinant Hansenula polymorpha as a biocatalyst. Coexpression of the spinach glycolate oxidase (GO) and the *S. cerevisiae* catalase T (CTT1) gene, Appl. Microbiol. Biotechnol. 46, 46-54; Farwick, M.; London, M.; Dohmen, J.; Dahlems, U.; Gellissen, G.; Strasser, A. W.; DE19920712). The preparation of such a whole cell catalyst is sufficiently well known to the person skilled in the art (Sambrook, J.; Fritsch, E. F. and Maniatis, T. (1989), Molecular cloning: a laboratory manual, $2^{nd}$ ed., Cold Spring Harbor Laboratory Press, New York; Balbas, P. and Bolivar, F. (1990), Design and construction of expression plasmid vectors in *E. coli*, Methods Enzymol. 185, 14-37; Rodriguez, R. L. and Denhardt, D. T (eds) (1988), Vectors: a survey of molecular cloning vectors and their uses, 205-225, Butterworth, Stoneham).

In a next embodiment, the invention relates to plasmids or vectors containing one or more of the nucleic acid sequences according to the invention.

Suitable plasmids or vectors are in principle any forms available to the person skilled in the art for this purpose. Such plasmids and vectors will be found, for example, in Studier et al. (Studier, W. F.; Rosenberg A. H.; Dunn J. J.; Dubendroff J. W.; (1990), Use of the T7 RNA polymerase to direct expression of cloned genes, Methods Enzymol. 185, 61-89) or the brochures of Novagen, Promega, New England Biolabs, Clontech or Gibco BRL. Further preferred plasmids and vectors can be found in: Glover, D. M. (1985), DNA cloning: a practical approach, Vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, $2^{nd}$ ed., Cold Spring Harbor Laboratory Press, New York.

Plasmids with which the gene construct containing the nucleic acid according to the invention can be cloned into the host organism in a very preferred manner are derivatives of pUC18 and pUC19 (Roche Biochemicals), pKK-177-3H (Roche Biochemicals), pBTac2 (Roche Biochemicals), pKK223-3 (Amersham Pharmacia Biotech), pKK-233-3 (Stratagene) or pET (Novagen). Further preferred plasmids are pBR322 (DSM3879), pACYC184 (DSM4439) and PSC101 (DSM6202), which can be obtained from DSMZ-Deutsche Sammlung von Mikroorganismen und Zellkulturen GmbH, Braunschweig, Germany.

The invention is likewise directed towards microorganisms containing one or more nucleic acid sequences according to the invention. The microorganism into which the plasmids containing the nucleic acid sequences according to the invention are cloned serves to multiply and obtain a sufficient amount of the recombinant enzyme. The processes therefor are well known to the person skilled in the art (Saxbrook, J.; Fritsch, E. F. and Maniatis, T. (1989), Molecular cloning: a laboratory manual, $2^{nd}$ ed., Cold Spring Harbor Laboratory Press, New York). In principle, there can be used as microorganisms any organisms suitable to the person skilled in the art for this purpose, such as, for example, yeasts, such as *Hansenula polymorpha*, *Pichia* sp., *Saccharomyces cerevisiae*, prokaryotes, such as *E. coli*, *Bacillus subtilis*, or eukaryotes, such as mammalian cells, insect cells. *E. coli* strains are preferably to be used for this purpose. Very particular preference is given to: *E. coli* XL1 Blue, W3110, DSM14459 (PCT/US00/08159), NM 522, JM101, JM109, JM105, RR1, DH5α, TOP 10⁻ and HB101. Plasmids with which the gene construct containing the nucleic acid according to the invention is preferably cloned into the host organism are indicated above.

A following aspect of the invention is directed towards primers for the preparation of the gene sequences according to the invention by means of any type of PCR. Included are the sense and antisense primers coding for the corresponding amino acid sequences, or complementary DNA sequences. Suitable primers can in principle be obtained by processes known to the person skilled in the art. The location of the primers according to the invention is carried out by comparison with known DNA sequences or by translation of the amino acid sequences under consideration into the preferred codon of the organism in question (e.g. for Streptomyces: Wright F. and Bibb M. J. (1992), Codon usage in the G+C-rich *Streptomyces* genome, Gene 113, 55-65). Similarities in the amino acid sequence of proteins of so-called superfamilies are likewise of use therefor (Firestine, S. M.; Nixon, A. E.; Benkovic, S. J. (1996), Threading your way to protein function, Chem. Biol. 3, 779-783). Further information hereon can be found in Gait, M. J. (1984), Oligonucleotide synthesis: a practical approach, IRL Press Ltd., Oxford; Innis, M. A.; Gelfound, D. H.; Sninsky, J. J. and White, T. J. (1990), PCR Protocols: A guide to methods and applications, Academic Press Inc., San Diego.

Preferred primers are those of Seq.ID.No. 11 and 12.

As already indicated, the enzymes under consideration (hydantoin racemase, hydantoinases and/or carbamoylases) can be used in free form as homogeneously purified compounds or as an enzyme prepared by recombinant methods (rec-). The enzymes may also be used as a constituent of an intact guest organism or in conjunction with the cell mass of the host organism which has been opened up and highly purified as desired.

It is also possible to use the enzymes in immobilised form (Sharma B. P.; Bailey L. F. and Messing R. A. (1982), Immobilisierte Biomaterialiern—Techniken und Anwendungen, Angew. Chem. 94, 836-852). Immobilisation is preferably carried out by lyophilisation (Paradkar, V. M.; Dordick, J. S. (1994), Aqueous-Like Activity of α-Chymotrypsin Dissolved in Nearly Anhydrous Organic Solvents, J. Am. Chem. Soc. 116, 5009-5010; Mori, T.; Okahata, Y. (1997), A variety of lipi-coated glycoside hydrolases as effective glycosyl transfer catalysts in homogeneous organic solvents, Tetrahedron Lett. 38, 1971-1974; Otamiri, M.; Adlercreutz, P.; Matthiasson, B. (1992), Complex formation between chymotrypsin and ethyl cellulose as a means to solbilize the enzyme in active form in toluene, Biocatalysis 6, 291-305). Very special preference is given to lyophilisation in the presence of surface-active substances, such as Aerosol OT or polyvinylpyrrolidone or polyethylene glycol (PEG) or Brij 52 (diethylene glycol monocetyl ether) (Kamiya, N.; Okazaki, S.-Y.; Goto, M. (1997), Surfactant-horseradish peroxidase complex catalytically active in anhydrous benzene, Biotechnol. Tech. 11, 375-378).

Very special preference is given to immobilisation on Eupergit®, especially Eupergit C® and Eupergit 250L® (Röhm) (Eupergit.RTM. C, a carrier for immobilization of enzymes of industrial potential. Katchalski-Katzir, E.; Kraemer, D. M. Journal of Molecular Catalysis B: Enzymatic (2000), 10(1-3), 157-176.)

Also preferred is immobilisation on Ni—NTA in combination with the polypeptide supplemented with the His tag (hexa-histidine) (Purification of proteins using polyhistidine affinity tags. Bornhorst, Joshua A.; Falke, Joseph J. Methods in Enzymology (2000), 326, 245-254). Use as CLECs is also conceivable (St. Clair, N.; Wang, Y.-F.; Margolin, A. L. (2000), Cofactor-bound cross-linked enzyme crystals (CLEC) of alcohol dehydrogenase, Angew. Chem. Int. Ed. 39, 380-383).

By means of these measures it can be possible to generate from polypeptides that are rendered unstable by organic solvents polypeptides that are stable and can work in mixtures of aqueous and organic solvents or in wholly organic solvents.

Whole cell catalysts are generally used in the form of free or immobilised cells. For this purpose, the active cell mass is re-suspended in a hydantoin-containing solution. The cell concentration is from 1 to 100 g/l. The concentration of hydantoin is from 0.1 to 2 molar. $H_2O$ is preferably used as the solvent, but mixtures of organic solvents and $H_2O$ can also be used. The pH value is either not controlled or is maintained between pH 6 and pH 10 by means of conventional buffers or by continuous pH monitoring. The reaction temperature is typically from 20° C. to 90° C. In dependence on the hydantoinase used, divalent metal ions are added in concentrations of from 0.1 to 5 mM. Preferred metal ions are $Mn^{2+}$, $Zn^{2+}$ or $Co^{2+}$. With regard to the use of the individual enzymes, an equivalent procedure can be employed.

The products prepared by the use of the hydantoin racemases according to the invention in the manner as described, for example, above are worked up by conventional methods. However, working up by ion exchange chromatography is preferred. As a result, the product is freed of the salts formed in the reaction. The eluate is optionally clarified using activated carbon and the resulting enantiomerically enriched amino acid or N-carbamoyl-amino acid is precipitated by concentration of the solvent and dried.

Coupling of an enzymatic racemisation with an enantioselective hydrolysis for the screening of hydantoin racemase activities has not hitherto been used to produce improved hydantoin racemases. For the process according to the invention to be applied particularly successfully, several requirements should be met:

1. The chemical racemisation rate of the enantiomerically pure hydantoin used in the screeing must be very much lower than the rate of the enzymatically catalysed reaction.
2. The enantioselective hydrolysis by means of the hydantoinase must take place very much more rapidly than the enzymatic racemisation of the hydantoin.

For aliphatically substituted hydantoins, point 1 is met owing to their slow chemical racemisation. Point 2 can be fulfilled by a targeted selection of suitable hydantoinases (see hereinabove).

The present invention is not rendered obvious by the statements made in the prior art, because no indications are to be found therein relating to the requirements mentioned hereinbefore.

All the indicated mutants exhibit a mutation at amino acid position 79, which for the first time indicates the importance of this position for the enzyme function. It is interesting that the amino acids surrounding this position are retained completely for all known hydantoin racemases. This shows that, for other hydantoin racemases which contain the above-described sequence motif and exhibit a high degree of homology (>40% sequence identity), improved enzyme variants can be produced by site-specific mutagenesis at position 79, which could not hitherto be derived from the prior art.

Within the scope of the invention, the expression optically enriched (enantiomerically enriched) compounds is understood to mean the presence of one optical antipode in admixture with the other in >50 mol. %.

The expression nucleic acid sequences includes all types of single-strand or double-strand DNA as well as RNA or mixtures thereof.

According to the invention, the improvement in the activity and/or selectivity and/or stability means that the polypeptides are more active and/or more selective or less selective or more stable under the reaction conditions.

While the activity and the stability of the enzymes should naturally be as high as possible for technical application, the selectivity is said to be improved when either the substrate selectivity falls but the enantioselectivity of the enzymes is increased.

According to the invention, the claimed polypeptides and the nucleic acid sequences also include those sequences which exhibit a homology (excluding natural degeneration) of greater than 70% (in respect of the nucleic acid sequence) or >40% or 80% (in respect of the polypeptides), preferably greater than 90%, 91%, 92%, 93% or 94%, more preferably greater than 95% or 96% and particularly preferably greater than 97%, 98% or 99%, with one of these sequences, provided that the mode of action or purpose of such a sequence is retained. The expression "homology" (or identity) as used herein can be defined by the equation H (%)=[1−V/X]×100, where H means homology, X is the total number of nuclebbases/amino acids in the comparison sequence and V is the number of different nucleobases/amino acids of the sequence under consideration relative to the comparison sequence. In any case, the expression nucleic acid sequences coding for polypeptides includes all sequences that appear possible according to the degeneration of the genetic code.

The expression "under stringent conditions" is understood herein as described in Sambrook et al. (Sambrook, J.; Fritsch, E. F. and Maniatis, T. (1989), Molecular cloning: a laboratory manual, $2^{nd}$ ed., Cold Spring Harbor Laboratory Press, New York). A stringent hybridisation according to the present invention is preferably present when, after washing for one hour with 1×SSC (150 mM sodium chloride, 15 mM sodium citrate, pH 7.0) and 0.1% SDS (sodium dodecylsulfate) at 50° C., preferably at 55° C., more preferably at 62° C. and most preferably at 68° C., and more preferably for 1 hour with 0.2×SSC and 0.1% SDS at 50° C., more preferably at 55° C., yet more preferably at 62° C. and most preferably at 68° C., a positive hybridisation signal is still observed.

The literature references cited in this specification are incorporated in the disclosure by reference.

The organism Arthrobacter aurescens DSM3747 was deposited with Deutsche Sammlung für Mikroorganismen GmbH, Mascheroder Weg 1b, 38124 Braunschweig by Rütgerswerke Aktiengesellschaft on 28.05.86.

EXAMPLES

Example 1

Production of Hydantoin Racemase Mutants—Random Mutagenesis 0.25 ng of the vector pOM21 (plasmid map see FIG. 1; sequence see Seq.ID.No.13) (PCT/US00/08159) was used as template in a 100 μl PCR reaction mix consisting of PCR buffer (10 mM Tris, 1.5 mM MgCl2, 50 mM KCl, pH 8.5), 200 μM dTTP, 200 μM dGTP, 200 μM dATP, 200 μM dCTP, 50 pmol. of the respective primer (see Seq.ID.No. 11 and 12) and 2.5 U Taq polymerase (Roche). After 30 cycles, the amplified product was purified by means of gel extraction (QiaexII gel extraction kit) and subcloned into the vector pOM21 by means of the restriction enzymes NdeI and PstI. The ligation product was used for the transformation of hydantoinase-positive strains (see Example 2).

Example 2

Preparation of Hydantoinase-Positive Strains and of a Mutant Library

Figure 2:
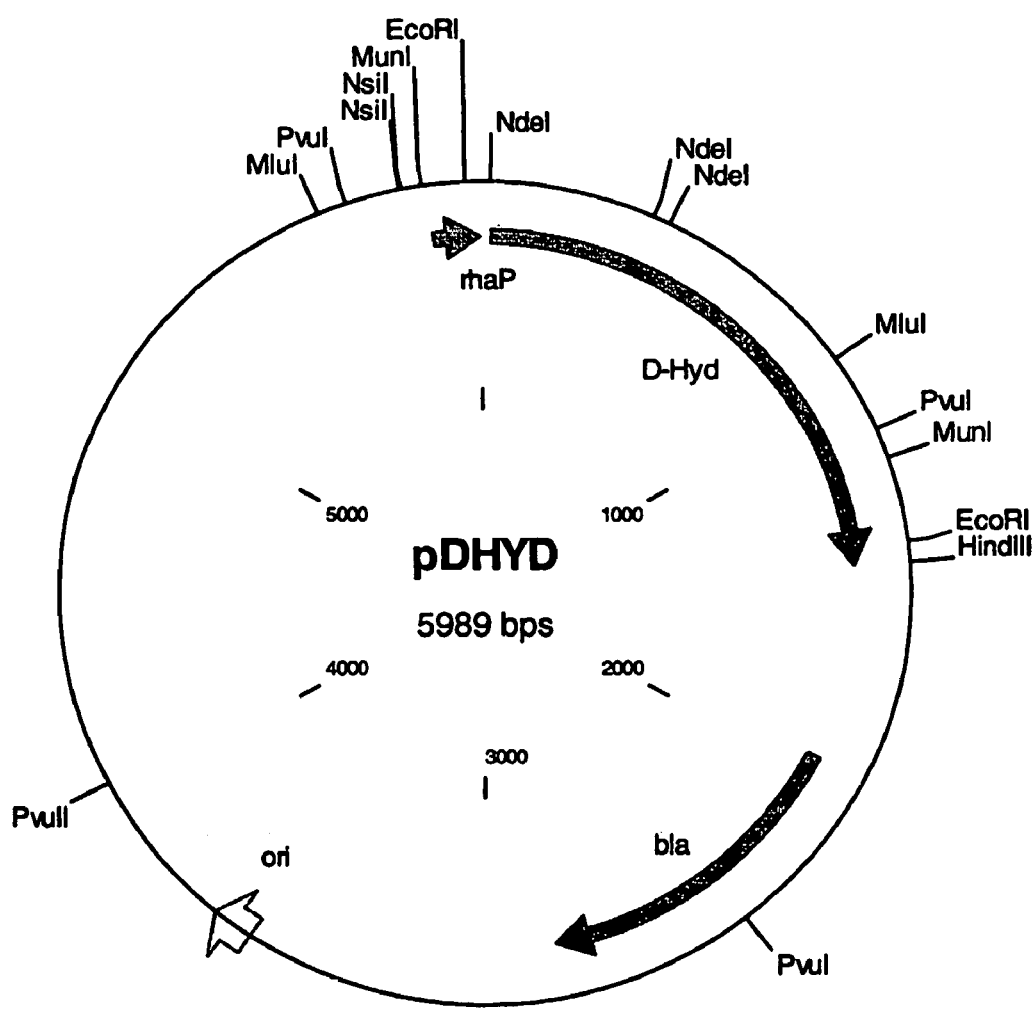

Chemically competent E. coli JM109 (e.g. from Promega) were transformed with 10 ng of the plasmid pDHYD (see FIG. 2; see Seq.ID.No. 15), which carries the D-hydantoinase gene from Arthrobacter crystallopoietes DSM20117 under the control of a rhamnose promoter. The complete sequence of the plasmid is shown in Seq.ID.No. 15. The hydantoinase-positive strain so produced was in turn rendered chemically competent and transformed for the preparation of the mutant library with the ligation product of the hydantoin racemase random mutagenesis from Example 1. The colonies of the mutant library were spread onto ampicillin- and chloramphenicol-containing agar plates and then subjected to a screening, which is described in Example 3.

Example 3

Screening for Hydantoin Racemase Mutants Having Improved Enzyme Properties

Individual colonies of the mutant library were inoculated in 96-well plates which were filled with 100 μl per well of LB medium (5 g/l yeast extract, 10 g/l trypton, 10 g/l NaCl) supplemented with rhamnose (2 g/l) and ZnCl$_2$ (1 mM). The plates were incubated for 20 hours at 30° C., 100 μl of screening substrate (100 mM L-ethylhydantoin, 50 mg/l cresol red, pH 8.5) were then added to each well and the plates were incubated for 4 hours at 20° C. Wells having improved hydantoin racemase mutants could be identified directly with the eye by means of a more intense yellow colouration compared with the wild type, or using a spectral photometer at 580 nm.

Example 4

Characterisation of Hydantoin Racemase Mutants Having Improved Enzyme Properties The racemase mutants identified in the screening were subsequently tested by means of HPLC analysis for their activity in comparison with the wild type, and the corresponding mutations were determined by means of sequencing. For this purpose, plasmids were isolated from individual colonies of the different clones (Qiagen Mini-Prep Kit) and sequenced. The same clones were used to produce active biomass. An overnight culture (OD$_{600}$=4) of the respective clones was to this end diluted 1:100 in 100 ml of LB medium (5 g/l yeast extract, 10 g/l trypton, 10 g/l NaCl) supplemented with rhamnose (2 g/l) and ZnCl$_2$ (1 mM) and incubated for 18 hours at 30° C. and 250 rpm. The biomass was pelletised by centrifugation (10 min, 10,000 g) and the supernatant was discarded. 2 g of active biomass were then re-suspended in 50 ml of the substrate solution (100 mM L-ethylhydantoin, pH 8.5) and incubated at 37° C. Samples were taken after various times, the biomass was separated off by centrifugation (5 min, 13,000 rpm) and the supernatant was analysed by means of HPLC for the concentration of the N-carbamoyl-aminobutyric acid formed.

Example 5

Preparation of L-Amino Acids Using Improved Hydantoin Racemases

Figure 3:
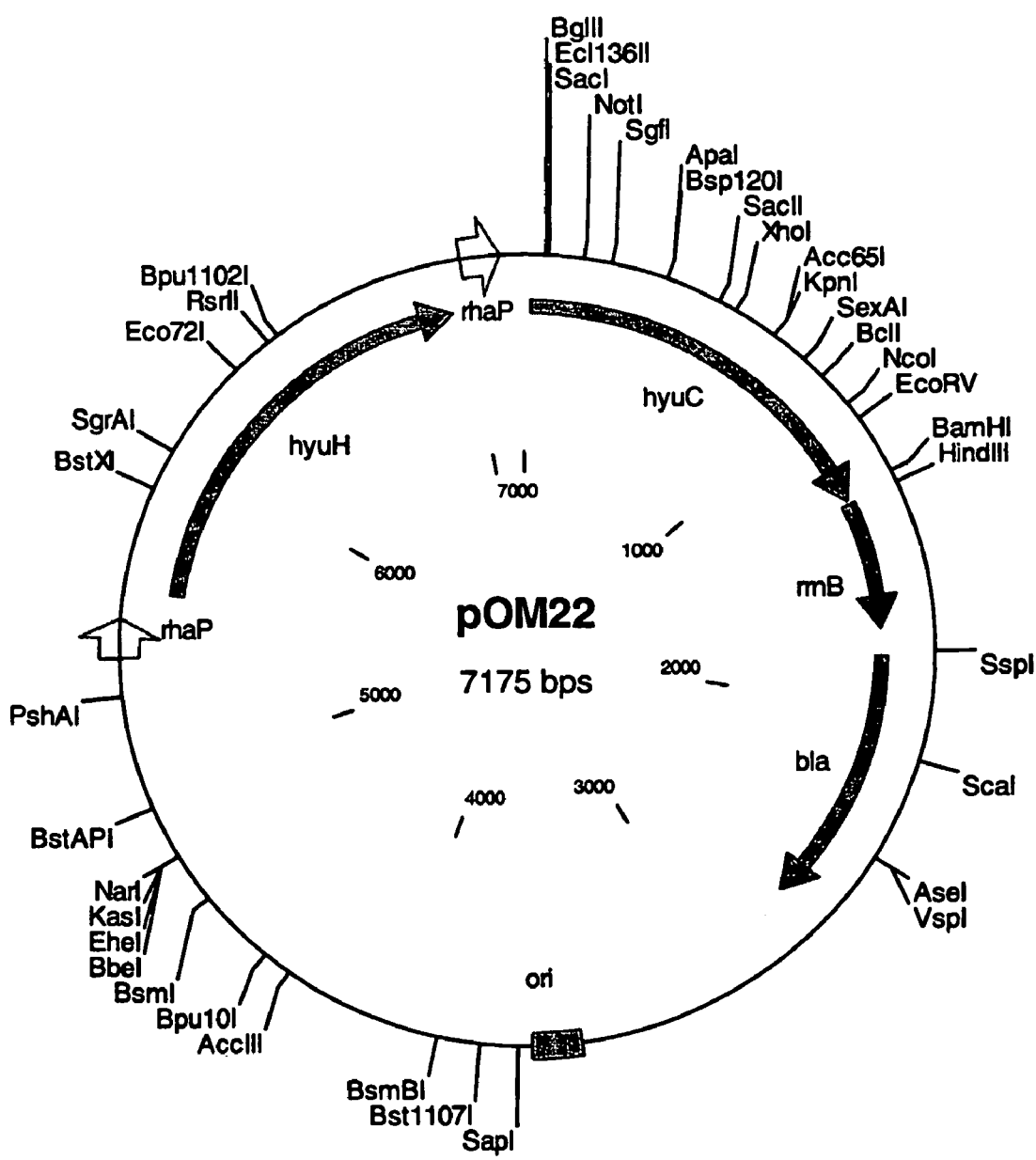

A strain of E. coli JM109 transformed with pOM21-BB5 and pOM22 FIG. 3 (see Seq.ID.No.14) (PCT/US00/08159) was incubated at 30° C. for 18 hours, with shaking (250 rpm), in LB medium which contained ampicillin (100 μg/l) and chloramphenicol (50 μg/l) and to which 2 g/l of rhamnose had been added. The biomass was pelletised by centrifugation and re-suspended in a corresponding volume of 100 mM DL-ethylhydantoin solution, pH 8.5, and 1 mM CoCl$_2$, so that a cell concentration of 30 g/l was obtained. This reaction solution was incubated for 10 hours at 37° C. The cells were then separated off by centrifugation (30 min, 5000 g) and the clear supernatant was analysed by means of HPLC for the resulting amino acid. For working up the resulting amino acid, the volume of the supernatant was reduced to half, and methanol was added 1:2. The precipitated amino acid was then filtered off and dried. The total yield of the amino acid was >60%.

Example 6

Preparation of D-Amino Acids Using Improved Hydantoin Racemases

Figure 4:
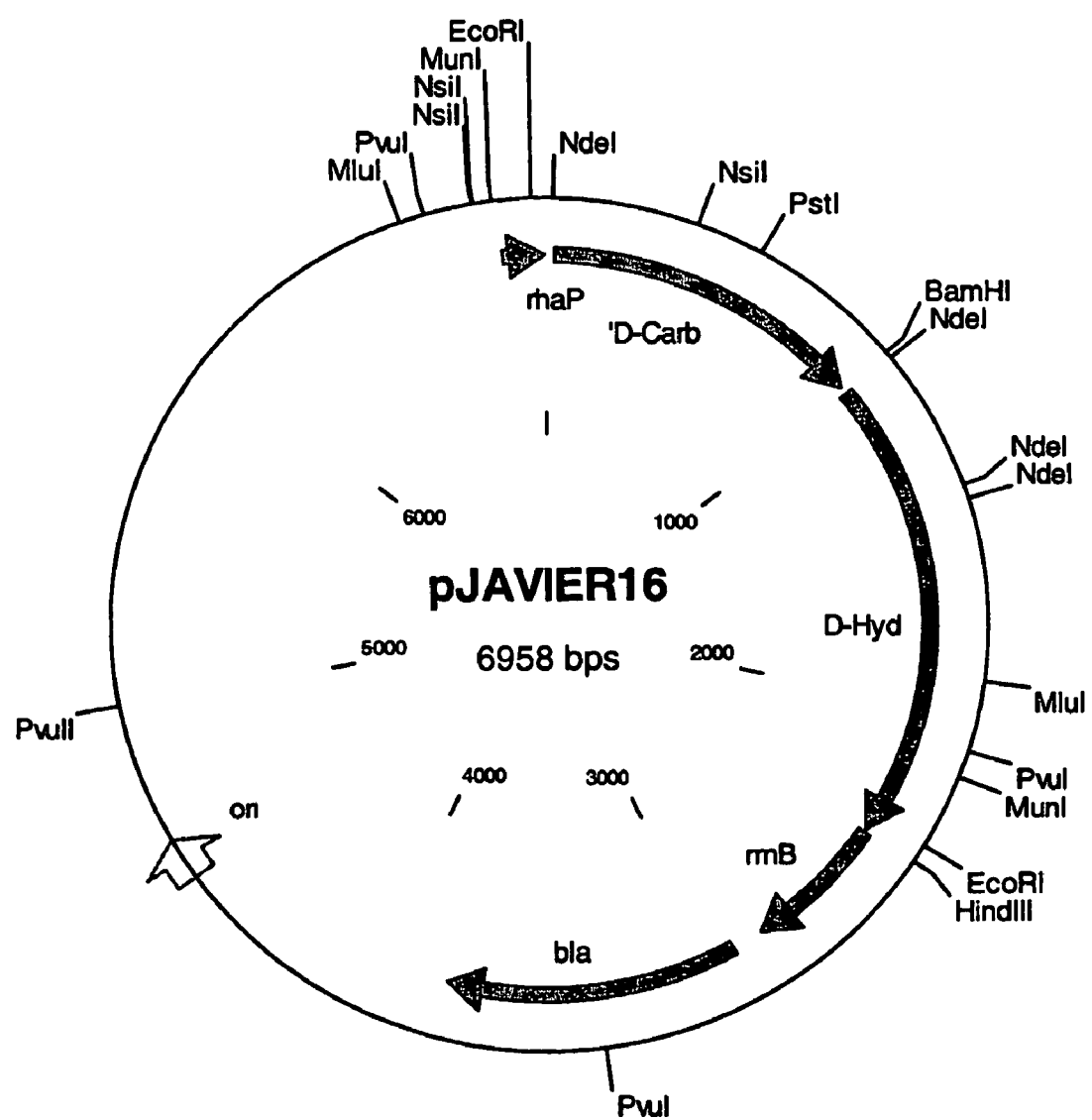

A strain of *E. coli* JM109 transformed with pOM21-BB5 and pJAVIER16 FIG. 4 (see Seq.ID.No.16) was incubated at 30° C. for 18 hours, with shaking (250 rpm), in LB medium which contained ampicillin (100 µg/l) and chloramphenicol (50 µg/l) and to which 2 g/l of rhamnose had been added. The biomass was pelletised by centrifugation and re-suspended in a corresponding volume of 100 mM DL-ethylhydantoin solution, pH 8.5, and 1 mM $CoCl_2$, so that a cell concentration of 30 g/l was obtained. This reaction solution was incubated for 10 hours at 37° C. The cells were then separated off by centrifugation (30 min, 5000 g) and the clear supernatant was analysed by means of HPLC for the resulting amino acid. For working up the resulting amino acid, the volume of the supernatant was reduced to half, and methanol was added 1:2. The precipitated amino acid was then filtered off and dried. The total yield of the amino acid was >60%.

What is claimed is:

1. An isolated, mutated hydantoin racemase, comprising the amino acid sequence of SEQ ID NO:2 but wherein the the amino acids at positions 78-83 in SEQ ID NO:2 are: FX$_1$DX$_2$GL (SEQ ID NO:1), wherein X$_2$ represents P or T and X$_1$ is at position 79 and is an amino acid selected from the group consisting of: A, R, N, D, C, Q, E, H, I, L, K, M, F, P, S, T, Y and V.

2. The mutated hydantoin racemase of claim 1, wherein the amino acid at position 79 is A.

3. The mutated hydantoin racemase of claim 1, wherein the amino acid at position 79 is R.

4. The mutated hydantoin racemase of claim 1, wherein the amino acid at position 79 is N.

5. The mutated hydantoin racemase of claim 1, wherein the amino acid at position 79 is D.

6. The mutated hydantoin racemase of claim 1, wherein the amino acid at position 79 is C.

7. The mutated hydantoin racemase of claim 1, wherein the amino acid at position 79 is Q.

8. The mutated hydantoin racemase of claim 1, wherein the amino acid at position 79 is E.

9. The mutated hydantoin racemase of claim 1, wherein the amino acid at position 79 is H.

10. The mutated hydantoin racemase of claim 1, wherein the amino acid at position 79 is I.

11. The mutated hydantoin racemase of claim 1, wherein the amino acid at position 79 is K.

12. The mutated hydantoin racemase of claim 1, wherein the amino acid at position 79 is L.

13. The mutated hydantoin racemase of claim 1, wherein the amino acid at position 79 is M.

14. The mutated hydantoin racemase of claim 1, wherein the amino acid at position 79 is F.

15. The mutated hydantoin racemase of claim 1, wherein the amino acid at position 79 is P.

16. The mutated hydantoin racemase of claim 1, wherein the amino acid at position 79 is S.

17. The mutated hydantoin racemase of claim 1, wherein the amino acid at position 79 is T.

18. The mutated hydantoin racemase of claim 1, wherein the amino acid at position 79 is Y.

19. The mutated hydantoin racemase of claim 1, wherein the amino acid at position 79 is V.

20. A method of making enantiomerically enriched N-carbamoyl-amino acids or amino acids comprising reacting hydantoin molecules with a hydantoinase and with the mutated hydantoin racemase of claim 1.

* * * * *